United States Patent [19]

Hitz et al.

[11] Patent Number: 5,760,206

[45] Date of Patent: *Jun. 2, 1998

[54] NUCLEOTIDE SEQUENCE OF SOYBEAN STEAROYL-ACP DESATURASE GENE

[75] Inventors: William D. Hitz; Narendra S. Yadav; Luis Perez-Grau, all of Wilmington, Del.

[73] Assignee: E. I. du Pont de Nemours and Company, Wilmington, Del.

[*] Notice: The term of this patent shall not extend beyond the expiration date of Pat. No. 5,443,974.

[21] Appl. No.: 474,587

[22] Filed: Jun. 7, 1995

Related U.S. Application Data

[63] Continuation-in-part of Ser. No. 995,657, Dec. 11, 1992, Pat. No. 5,443,974, which is a continuation-in-part of PCT/US91/03288, filed May 19, 1991.

[51] Int. Cl.$^6$ .......................... C12N 15/11; C12N 15/00; C12N 5/14
[52] U.S. Cl. .......................... 536/23.6; 536/23.1; 536/23.2; 935/22; 935/23; 935/35; 935/67; 800/205; 435/172.3; 435/172.1; 435/69.1
[58] Field of Search .......................... 435/172.1, 172.3, 435/69.1, 692; 935/22, 23, 35, 42; 536/23.1, 23.2, 23.6; 800/205

[56] References Cited

U.S. PATENT DOCUMENTS 5,443,974  8/1995  Hitz et al. .......................... 435/172.3

FOREIGN PATENT DOCUMENTS 0193259  9/1986  European Pat. Off. ............ 435/172.3
9113972  9/1991  WIPO .......................... 435/172.3

OTHER PUBLICATIONS

Kinney et al. Stearoyl-ACP desaturase and a B-ketoacyl-ACP synthetase from developing soybean seeds. Plant Lipid Biochemistry, Structure and Utilization. The proceedings of the Ninth International Symposium on plant Lipids, held ay Wye College, Kent. pp. 126–128, Aug. 8, 1990.

Lewin "Science" vol. 237 pp. 1570, 1987.

Knauf V. TIBECH. vol. 85 pp. 40–47, 1987.

van de Krol et al. "Gene" vol. 72 pp. 45–50, 1988.

Shanklin et al. PNAS vol. 88 pp. 2510–2514, 1991.

Knutzon et al. PNAS vol. 89 pp. 2624–2628, 1992.

*Primary Examiner*—Gary Benzion

[57] ABSTRACT

The preparation and use of nucleic acid fragments encoding soybean seed stearoyl-ACP desaturase enzyme or its precursor to modify plant oil composition are described. Chimeric genes incorporating such nucleic acid fragments and suitable regulatory sequences may be utilized to transform plants to control the levels of saturated and unsaturated fatty acids.

5 Claims, No Drawings

NUCLEOTIDE SEQUENCE OF SOYBEAN STEAROYL-ACP DESATURASE GENE

This application is a continuation-in-part of U.S. Ser. No. 07/995,657 filed Dec. 11, 1992, now U.S. Pat. No. 5,413,974 which is a continuation-in-part of International Application No. PCT/US91/03288 filed May 19, 1991, which claims priority to U.S. Ser. No. 07/529,049, filed May 25, 1990, now abandoned.

BACKGROUND OF THE INVENTION

Soybean oil accounts for about 70% of the 14 billion pounds of edible oil consumed in the United States and is a major edible oil worldwide. It is used in baking, frying, salad dressing, margarine, and a multitude of processed foods. In 1987/88 60 million acres of soybean were planted in the U.S. Soybean is the lowest-cost producer of vegetable oil, which is a by-product of soybean meal. Soybean is agronomically well-adapted to many parts of the U.S. Machinery and facilities for harvesting, storing, and crushing are widely available across the U.S. Soybean products are also a major element of foreign trade since 30 million metric tons of soybeans, 25 million metric tons of soybean meal, and 1 billion pounds of soybean oil were exported in 1987/88. Nevertheless, increased foreign competition has lead to recent declines in soybean acreage and production. The low cost and ready availability of soybean oil provides an excellent opportunity to upgrade this commodity oil into higher value speciality oils to both add value to soybean crop for the U.S. farmer and enhance U.S. trade.

Soybean oil derived from commercial varieties is composed primarily of 11% palmitic (16:0), 4% stearic (18:0), 24% oleic (18:1), 54% linoleic (18:2) and 7% linolenic (18:3) acids. Palmitic and stearic acids are, respectively, 16- and 18-carbon-long saturated fatty acids. Oleic, linoleic and linolenic are 18-carbon-long unsaturated fatty acids containing one, two and three double bonds, respectively. Oleic acid is also referred to as a monounsaturated fatty acid, while linoleic and linolenic acids are also referred to as polyunsaturated fatty acids. The specific performance and health attributes of edible oils is determined largely by their fatty acid composition.

Soybean oil is high in saturated fatty acids when compared to other sources of vegetable oil and contains a low proportion of oleic acid, relative to the total fatty acid content of the soybean seed. These characteristics do not meet important health needs as defined by the American Heart Association.

More recent research efforts have examined the role that monounsaturated fatty acid plays in reducing the risk of coronary heart disease. In the past, it was believed that monounsaturates, in contrast to saturates and polyunsaturates, had no effect on serum cholesterol and coronary heart disease risk. Several recent human clinical studies suggest that diets high in monounsaturated fat may reduce the "bad" (low-density lipoprotein) cholesterol while maintaining the "good" (high-density lipoprotein) cholesterol. [See Mattson et al. (1985) Journal of Lipid Research 26:194–202, Grundy (1986) New England Journal of Medicine 314:745–748, and Mensink et al.(1987) The Lancet 1:122–125, all collectively herein incorporated by reference.] These results corroborate previous epidemiological studies of people living in Mediterranean countries where a relatively high intake of monounsaturated fat and low consumption of saturated fat correspond with low coronary heart disease mortality. [Keys, A., Seven Countries: A Multivariate Analysis of Death and Coronary Heart Disease, Cambridge: Harvard University Press, 1980, herein incorporated by reference.] The significance of monounsaturated fat in the diet was further confirmed by international researchers from seven countries at the Second Colloquim on Monounsaturated Fats held Feb. 26, 1987, in Bethesda, Md., and sponsored by the National Heart, Lung and Blood Institutes [Report, Monounsaturates Use Said to Lower Several Major Risk Factors, Food Chemical News, Mar. 2, 1987, p. 44, herein incorporated by reference].

Soybean oil is also relatively high in polyunsaturated fatty acids—at levels in far excess of our essential dietary requirement. These fatty acids oxidize readily to give off-flavors and result in reduced performance associated with unprocessed soybean oil. The stability and flavor of soybean oil is improved by hydrogenation, which chemically reduces the double bonds. However, the need for this processing reduces the economic attractiveness of soybean oil.

A soybean oil low in total saturates and polyunsaturates and high in monounsaturate would provide significant health benefits to the United States population, as well as, economic benefit to oil processors. Soybean varieties which produce seeds containing the improved oil will also produce valuable meal as animal feed.

Another type of differentiated soybean oil is an edible fat for confectionary uses. More than 2 billion pounds of cocoa butter, the most expensive edible oil, are produced worldwide. The U.S. imports several hundred million dollars worth of cocoa butter annually. The high and volatile prices and uncertain supply of cocoa butter have encouraged the development of cocoa butter substitutes. The fatty acid composition of cocoa butter is 26% palmitic, 34% stearic, 35% oleic and 3% linoleic acids. About 72% of cocoa butter's triglycerides have the structure in which saturated fatty acids occupy positions 1 and 3 and oleic acid occupies position 2. Cocoa butter's unique fatty acid composition and distribution on the triglyceride molecule confer on it properties eminently suitable for confectionary end-uses: it is brittle below 27° C. and depending on its crystalline state, melts sharply at 25°–30° C. or 35°–36° C. Consequently, it is hard and non-greasy at ordinary temperatures and melts very sharply in the mouth. It is also extremely resistant to rancidity. For these reasons, producing soybean oil with increased levels of stearic acid, especially in soybean lines containing higher-than-normal levels of palmitic acid, and reduced levels of unsaturated fatty acids is expected to produce a cocoa butter substitute in soybean. This will add value to oil and food processors as well as reduce the foreign import of certain tropical oils.

Only recently have serious efforts been made to improve the quality of soybean oil through plant breeding, especially mutagenesis, and a wide range of fatty acid composition has been discovered in experimental lines of soybean (Table 1). These findings (as well as those with other oilcrops) suggest that the fatty acid composition of soybean oil can be significantly modified without affecting the agronomic performance of a soybean plant. However, there is no soybean mutant line with levels of saturates less than those present in commercial canola, the major competitor to soybean oil as a "healthy" oil.

TABLE 1

Range of Fatty Acid Percentages Produced by Soybean Mutants

| Fatty Acids | Range of Percentages |
| --- | --- |
| Palmitic Acid | 6–28 |
| Stearic Acid | 3–30 |
| Oleic Acid | 17–50 |
| Linoleic Acid | 35–60 |
| Linolenic Acid | 3–12 |

There are serious limitations to using mutagenesis to alter fatty acid composition. It is unlikely to discover mutations a) that result in a dominant ("gain-of-function") phenotype, b) in genes that are essential for plant growth, and c) in an enzyme that is not rate-limiting and that is encoded by more than one gene. Even when some of the desired mutations are available in soybean mutant lines their introgression into elite lines by traditional breeding techniques will be slow and expensive, since the desired oil compositions in soybean are most likely to involve several recessive genes.

Recent molecular and cellular biology techniques offer the potential for overcoming some of the limitations of the mutagenesis approach, including the need for extensive breeding. Particularly useful technologies are: a) seed-specific expression of foreign genes in transgenic plants [see Goldberg et al.(1989) Cell 56:149–160], b) use of antisense RNA to inhibit plant target genes in a dominant and tissue-specific manner [see van der Krol et al. (1988) Gene 72:45–50], c) transfer of foreign genes into elite commercial varieties of commercial oilcrops, such as soybean [Chee et al. (1989) Plant Physiol. 91:1212–1218; Christou et al. (1989) Proc. Natl. Acad. Sci. U.S.A. 86:7500–7504; Hinchee et al. (1988) Bio/Technology 6:915–922; EPO publication 0 301 749 A2], rapeseed [De Block et al. (1989) Plant Physiol. 91:694–701], and sunflower [Everett et al. (1987) Bio/Technology 5:1201–1204], and d) use of genes as restriction fragment length polymorphism (RFLP) markers in a breeding program, which makes introgression of recessive traits into elite lines rapid and less expensive [Tanksley et al. (1989) Bio/Technology 7:257–264]. However, application of each of these technologies requires identification and isolation of commercially-important genes.

Oil biosynthesis in plants has been fairly well-studied [see Harwood (1989) in Critical Reviews in Plant Sciences, Vol. 8(1):1–43]. The biosynthesis of palmitic, stearic and oleic acids occur in the plastids by the interplay of three key enzymes of the "ACP track": palmitoyl-ACP elongase, stearoyl-ACP desaturase and acyl-ACP thioesterase. Stearoyl-ACP desaturase introduces the first double bond on stearoyl-ACP to form oleoyl-ACP. It is pivotal in determining the degree of unsaturation in vegetable oils. Because of its key position in fatty acid biosynthesis it is expected to be an important regulatory step. While the enzyme's natural substrate is stearoyl-ACP, it has been shown that it can, like its counterpart in yeast and mammalian cells, desaturate stearoyl-CoA, albeit poorly [McKeon et al. (1982) J. Biol. Chem. 257:12141–12147]. The fatty acids synthesized in the plastid are exported as acyl-CoA to the cytoplasm. At least three different glycerol acylating enzymes (glycerol-3-P acyl-transferase, 1-acyl-glycerol-3-P acyltransferase and diacylglycerol acyltransferase) incorporate the acyl moieties from the cytoplasm into triglycerides during oil biosynthesis. These acyltransferases show a strong, but not absolute, preference for incorporating saturated fatty acids at positions 1 and 3 and monounsaturated fatty acid at position 2 of the triglyceride. Thus, altering the fatty acid composition of the acyl pool will drive by mass action a corresponding change in the fatty acid composition of the oil. Furthermore, there is experimental evidence that, because of this specificity, given the correct composition of fatty acids, plants can produce cocoa butter substitutes [Bafor et al. (1990) JAOCS 67:217–225].

Based on the above discussion, one approach to altering the levels of stearic and oleic acids in vegetable oils is by altering their levels in the cytoplasmic acyl-CoA pool used for oil biosynthesis. There are two ways of doing this genetically: a) altering the biosynthesis of stearic and oleic acids in the plastid by modulating the levels of stearoyl-ACP desaturase in seeds through either overexpression or anti-sense inhibition of its gene, and b) converting stearoyl-CoA to oleoyl-CoA in the cytoplasm through the expression of the stearoyl-ACP desaturase in the cytoplasm.

In order to use antisense inhibition of stearoyl-ACP desaturase in the seed, it is essential to isolate the gene(s) or cDNA(s) encoding the target enzyme(s) in the seed, since antisense inhibition requires a high-degree of complementarity between the antisense RNA and the target gene that is expected to be absent in stearoyl-ACP desaturase genes from other species.

The purification and nucleotide sequences of mammalian microsomal stearoyl-CoA desaturases have been published [Thiede et al. (1986) J. Biol. Chem. 262:13230–13235; Ntambi et al. (1988) J. Biol. Chem. 263:17291–17300; Kaestner et al. (1989) J. Biol. Chem. 264:14755–14761]. However, the plant enzyme differs from them in being soluble, in utilizing a different electron donor, and in its substrate-specificities. The purification and the nucleotide sequences for animal enzymes do not teach how to purify the plant enzyme or isolate a plant gene. The purification of stearoyl-ACP desaturase was reported from safflower seeds [McKeon et al. (1982) J. Biol. Chem. 257:12141–12147]. However, this purification scheme was not useful for soybean, either because the desaturases are different or because of the presence of other proteins such as the soybean seed storage proteins in seed extracts.

The rat liver stearoyl-CoA desaturase protein has been expressed in *E. coli* [Strittmatter et al. (1988) J. Biol. Chem. 263:2532–2535] but, as mentioned above, its substrate specificity and electron donors are quite distinct from that of the plant.

Plant stearoyl-ACP desaturase cDNAs have been cloned from safflower [Thompson et al. (1991) Proc. Natl. Acad. Sci. 88:2578], castor [Shanklin and Somerville (1991) Proc. Natl. Acad. Sci. 88:2510–2514], and cucumber [Shanklin et al. (1991) Plant Physiol. 97:467–468]. Kutzon et al. [(1992) Proc. Natl. Acad. Sci. 89:2624–2648] have reported that rapeseed stearoyl-ACP desaturase when expressed in *Brassica rapa* and *B. napa* in an antisense orientation can result in increase in 18:0 level in transgenic seeds.

SUMMARY OF THE INVENTION

A means to control the levels of saturated and unsaturated fatty acids in edible plant oils has been discovered. Utilizing the soybean seed stearoyl-ACP desaturase CDNA for either the precursor or enzyme, chimeric genes are created and may be utilized to transform various plants to modify the fatty acid composition of the oil produced. Specifically, one aspect of the present invention is a nucleic acid fragment comprising a nucleotide sequence encoding the soybean seed stearoyl-ACP desaturase cDNA corresponding to the nucleotides 1 to 2243 or more specifically 1 to 1552 in SEQ ID NO:1, or any nucleic acid fragment substantially homologous therewith. Preferred are those nucleic acid fragments encoding the soybean seed stearoyl-ACP desaturase precursor or the mature soybean seed stearoyl-ACP desaturase enzyme.

Another aspect of this invention involves a chimeric gene capable of transforming a soybean plant cell comprising a nucleic acid fragment encoding the soybean seed stearoyl-ACP desaturase cDNA operably linked to suitable regulatory sequences producing antisense inhibition of soybean seed stearoyl-ACP desaturase in the seed. Preferred are those chimeric genes which incorporate nucleic acid fragments encoding the soybean seed stearoyl-ACP desaturase precursor or the mature soybean seed stearoyl-ACP desaturase enzyme.

Yet another embodiment of the invention involves a method of producing seed oil containing modified or altered levels of saturated and unsaturated fatty acids comprising: (a) transforming a plant cell with a chimeric gene described above, (b) growing sexually mature plants from said transformed plant cells, (c) screening progeny seeds from said sexually mature plants for the desired levels of stearic acid, and (d) crushing said progeny seed to obtain said oil containing modified levels of stearic acid. Preferred plant cells and oils are derived from soybean, rapeseed, sunflower, cotton, cocoa, peanut, safflower, and corn. Preferred methods of transforming such plant cells would include the use of Ti and Ri plasmids of Agrobacterium, electroporation, and high-velocity ballistic bombardment.

DETAILED DESCRIPTION OF THE INVENTION

The present invention describes a nucleic acid fragment that encodes soybean seed stearoyl-ACP desaturase. This enzyme catalyzes the introduction of a double bond between carbon atoms 9 and 10 of stearoyl-ACP to form oleoyl-ACP. It can also convert stearoyl-CoA into oleoyl-CoA, albeit with reduced efficiency. Transfer of the nucleic acid fragment of the invention, or a part thereof that encodes a functional enzyme, with suitable regulatory sequences into a living cell will result in the production or over-production of stearoyl-ACP desaturase, which in the presence of an appropriate electron donor, such as ferredoxin, may result in an increased level of unsaturation in cellular lipids, including oil, in tissues when the enzyme is absent or rate-limiting.

Occasionally, reintroduction of a gene or a part thereof into a plant results in the inhibition of both the reintroduced and the endogenous gene, Jorgenson (December, 1990) Trends in Biotechnology 340–344. Therefore, reintroduction of the nucleic acid fragment of the invention is also expected to, in some cases, result in inhibition of the expression of endogenous seed stearoyl-ACP desaturase and would then result in increased level of saturation in seed oil.

Transfer of the nucleic acid fragment of the invention into a soybean plant with suitable regulatory sequences that transcribe the antisense RNA complementary to the mRNA, or its precursor, for seed stearoyl-ACP desaturase may result in the inhibition of the expression of the endogenous stearoyl-ACP desaturase gene and, consequently, in reduced desaturation in the seed oil.

The nucleic acid fragment of the invention can also be used as a restriction fragment length polymorphism marker in soybean genetic studies and breeding programs.

In the context of this disclosure, a number of terms shall be utilized. As used herein, the term "nucleic acid" refers to a large molecule which can be single stranded or double stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. The term "oligomer" refers to short nucleotide sequences, usually up to 100 bases long. As used herein, the term "homologous to" refers to the structural, not evolutionary, relatedness between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.); or by the comparison of sequence similarity between two nucleic acids or proteins, such as by the method of Needleman et al. (J. Mol. Biol. (1970) 48:443–453). As used herein, "substantially homologous" refers to nucleotide sequences that can be isolated by sequence-dependent protocols well known to one skilled in the art utilizing the claimed sequences and that can by their transformation into a plant cell alter its level of stearic acid. Substantially homologous sequences include those encoding stearoyl-ACP desaturase and its isozymes, those that involve base changes that do not cause a change in an encoded amino acid, those which involve base changes that alter an amino acid but do not affect the functional properties of the protein encoded by the DNA sequence, those that have an overall identity of 90% or more at the nucleotide level with the coding region of the claimed sequence, those which comprise possible variations, both man-made and natural, such as but not limited to those derived from deletions, rearrangements, amplifications, random or controlled mutagenesis of the nucelic acid fragment, and even occasional nucleotide sequencing errors. "Sequence-dependent protocols" refer to techniques that rely on a nucleotide sequence for their utility. Examples of sequence-dependent protocols include, but are not limited to, the methods of nucleic acid and oligomer hybridization and methods of DNA and RNA amplification such as are exemplified in various uses of the polymerase chain reaction.

"Gene" refers to a nucleic acid fragment that expresses a specific protein, including regulatory sequences preceding (5' non-coding) and following (3' non-coding) the coding region. "Stearoyl-ACP desaturase gene" refers to a nucleic acid fragment that expresses a protein with stearoyl-ACP desaturase activity. "Native" gene refers to the gene as found in nature with its own regulatory sequences. "Chimeric" gene refers to a gene that comprises heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is transcribed in the primary transcript but which is removed through cleavage and re-ligation of the RNA within the cell to create the mature mRNA that can be translated into a protein.

"Translation initiation codon" and "translation termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to an RNA transcr"Antisense RNA" refer mRNA. "Antisense RNA" refers to an RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that may increase the efficacy of antisense RNA to block gene expression. "Ribozyme" refers to a catalytic RNA and includes sequence-specific endoribonucleases.

As used herein, "suitable regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. In artificial DNA constructs, regulatory sequences can also control the transcription and stability of antisense RNA.

"Promoter" refers to a DNA sequence in a gene, usually upstream (5') to its coding sequence, which controls the expression of the coding sequence by providing the recognition for RNA polymerase and other factors required for proper transcription. In artificial DNA constructs promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively. "Inducible promoters" refers to those that direct gene expression in response to an external stimulus, such as light, heat-shock and chemical.

The term "expression", as used herein, refers to the transcription and stable accumulation of the sense (mRNA) or the antisense RNA derived from the nucleic acid fragment (s) of the invention that, in conjunction with the protein apparatus of the cell, results in altered levels of the stearoyl-ACP desaturase(s). Expression or overexpression of the gene involves transcription of the gene and translation of the mRNA into precursor or mature stearoyl-ACP desaturase proteins. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a foreign gene which has substantial homology to an endogenous gene resulting in the suppression of expression of both the foreign and the endogenous gene. "Altered levels" refers to the production of gene product(s) in transgenic organisms in amounts or proportions that differ in detectable amounts from that of normal or non-transformed organisms.

The "3' non-coding sequences" refers to that the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Mature" protein refers to a functional desaturase enzyme without its transit peptide. "Precursor" protein refers to the mature protein with a native or foreign transit peptide. The term "transit peptide" refers to the amino terminal extension of a polypeptide, which is translated in conjunction with the polypeptide forming a precursor peptide and which is required for its uptake by organelles such as plastids or mitochondria of a cell.

"Transformation" herein refers to the transfer of a foreign gene into the genome of a host organism and its genetically stable inheritance. "Restriction fragment length polymorphism" refers to different sized restriction fragment lengths due to altered nucleotide sequences in or around variant forms of genes, and may be abbreviated as "RFLP". "Fertile" refers to plants that are able to propagate sexually.

Purification of Soybean Seed Stearoyl-ACP
Desaturase

Stearoyl-ACP desaturase protein was purified to near-homogeneity from the soluble fraction of extracts made from developing soybean seeds following its chromatography on Blue Sepharose, anion-exchange, alkyl-ACP sepharose, and chromatofocussing on Mono P (Pharmacia). Because of the lability of the enzyme during purification, the nearly homogenous preparation is purified only ca. a few hundred-fold; the basis of this lability is not understood. Chromatofocussing resolved the enzyme into two peaks of activity: the peak that eluted earlier, with an apparent pI of ca. 6, had a higher specific-activity than the peak eluting later, with an apparent pI of ca. 5.7. The native molecular weight of the purified enzyme was estimated by gel filtration to be ca. 65 kD. SDS-polyacrylamide gel electrophoresis (SDS-PAGE) of the purified desaturase preparation showed it to be a polypeptide of ca. 38 kD, which suggests that the native enzyme is a dimer. A smaller polypeptide is occasionally observed in varying amounts resulting in a doublet in some preparations. This appears to be due to a proteolytic breakdown of the larger one, since the level of the smaller one increases during storage. However, it cannot be ruled out that the enzyme could also be a heterodimer or that there are different-sized isozymes.

A highly purified desaturase preparation was resolved on SDS-PAGE, electrophoretically transferred onto Immobilon®-P membrane (Millipore), and stained with Coomassie blue. The ca. 38 kD protein on the Immobilon®-P was cut out and used to make polyclonal antibody in mice.

A $C_4$ reverse-phase HPLC column was used to further purify the enzyme that eluted earlier in chromato-focussing. The major protein peak was homogeneous for the ca. 38 kD polypeptide. It was used for determining the N-terminal sequence: Arg-Ser-Gly-Ser-Lys-Glu-Val-Glu-Asn-Ile-Lys-Lys-Pro-Phe-Thr-Pro (SEQ ID NO:3).

Cloning of Soybean Seed Stearoyl-ACP Desaturase cDNA

Based on the N-terminal sequence of the purified desaturase protein, a set of eight degenerate 35 nucleotide-long oligonucleotides was designed for use as a hybridization probe. The design took into account the codon usage in selected soybean seed genes and used five deoxyinosines at selected positions of ambiguity. The probe, following radiolabeling, was used to screen a cDNA expression library made in Lambda ZAP vector from poly $A^+$ RNA from 20-day old developing soybean seeds. Six positively-hybridizing plaques were subjected to plaque purification. Sequences of the pBluescript (Stratagene) vector, including the cDNA inserts, from each of six purified phages were excised in the presence of a helper phage and the resultant phagemids used to infect E. coli cells resulting in a double-stranded plasmids, pDS1 to pDS6.

The cDNA insert in plasmid pDS1 is flanked at one end (the 5' end of the coding sequence) by the unique Eco RI site and at its other end by the unique Hind III site. Both Eco RI and the Hind III sites are from the vector, pBluescript. The nucleotide sequence of the cDNA insert in pDS1 revealed an open reading frame for 402 amino acids that included the mature protein's N-terminal sequence 43 amino acid residues from the N-terminus of the open reading frame (SEQ ID NO:1). At least part of this "presequence" is the transit peptide required for precursor import into the chloroplast. Although there are four methionines in this presequence that are in-frame with the mature protein sequence, the most likely N-terminal residue is methionine at position –32 (with the N-terminal Arg of mature protein being referred to as +1) since: a) the N-terminal methionine in the transit peptide sequences for all known chloroplast precursor proteins, with only one exception, is followed by alanine, and b) the methionine at position –5 is too close to the N-terminus of the mature protein to be the initiating codon for the transit peptide (the smallest transit sequence found thus far is 31 amino acids long). Thus, it can be deduced that the desaturase precursor protein consists of a 32-amino acid long transit peptide and a 359-amino acid long mature protein. Based on fusion-protein studies in which the C-terminus of foreign proteins is fused either to the desaturase precursor at position –10 (Ser) or to the mature desaturase protein at position +10 (Ile), the N-terminus of a functional stearoyl-ACP desaturase enzyme can range at least ±10 amino acids from Arg at position +1 (SEQ ID NO:1).

The restriction maps of all six plasmids, though not identical, showed a common 0.7 kb Bgl II fragment found within the coding region of the precursor for stearoyl-ACP desaturase in pDS1. This strongly suggests that all six clones encode for the stearoyl-ACP desaturase. The partial restriction maps of plasmids pDS1, pDS5 and pDS6 appear to be the identical. The inserts in pDS2 and pDS3, which differ in their physical maps from each other as well as from that of pDS1, were partially sequenced. Their partial nucleotide sequences, including 262 nucleotides from the 3' non-coding region, were identical to that in pDS1.

Of the several cDNA clones isolated from the soybean cDNA library using the cDNA insert in plasmid pDS1 as hybridization probe, five were sequenced in the 3' non-coding sequence and their sequences compared to that of SEQ ID NO:1. The results are summarized below:

| Clone # | Sequence correspondence to SEQ ID NO: 1 | Percent Identity |
|---|---|---|
| 1 | 1291–1552 | 100 |
| 2 | 1291–1394 | 100 |
| 3 | 1285–1552 | 100 |
| 4 | 1285–1552 | 100 |
| 5 | 1298–1505 | 92 |

Thus, while SEQ ID NO:1 most likely represents the predominantly-expressed stearoyl-ACP desaturase gene in soybean seed, at least one other stearoyl-ACP desaturase gene represented by clone #5 above, whose partial sequence is shown in SEQ ID NO:2, is expressed in the seed. It's full-length version can be readily isolated by one skilled in the art.

When the cDNA insert in pDS1 was isolated and used as a hybridization probe on a Southern blot of soybean genomic DNA following digestion with one of several restriction enzymes it hybridized to about 6 large fragments in most digests.

The cDNA insert in plasmid pDS1 (SEQ ID NO:1) has a nucleotide sequence 3' to the coding region that is surprisingly long for a cDNA. When it was used as a labeled hybridization probe on mRNA samples isolated from developing soybean seeds it hybridized to a 1.4 kB mRNA of an expected size as well as to a 0.9 kB mRNA of an expected size. This raised the possibility that plasmid pDS1 actually contains two independent cDNA inserts. Comparison of SEQ ID NO:1 with the nucleotides sequence in the GenBank database using the FASTA algorithm of Pearson and Lipman (Proc. Natl. Acad. Sci. USA (988) 85:2444–2448) revealed a significantly high degree of relatedness of the 3' region of pDS1 with the yeast (Saccharomyces cerevisiae) ribosomal protein S24 gene Genbank accession No. X01962). Analyses of the pDS1 region 3' to the stearoyl-ACP desaturase open reading frame revealed another open reading frame from nucleotides 1603 to 1995 (SEQ ID NO:1). Comparison of the deduced protein sequence encoded by the second open frame (nucleotides 1603 to 1995 SEQ ID NO:1) in 3' region of SEQ ID NO:1 with that encoded by yeast protein revealed 79% identity and 88% similarity at the amino acid level. Thus, it is likely that pDS1 is comprised of two distinct cDNAs. To delete the putative additional cDNA clone, plasmid pDS1 was digested with restriction enzymes Hind III and Nco I, the ends filled-in with Klenow, ligated, and then transformed into E. coli cells. Ampicillin-resistant transformants were analyzed by restriction digests. Plasmid DNA was purified from a transformant, designated pDS1S, with the correct sized fragments. The insert from pDS1S was isolated and used as a hybridization probe on both Northern and Southern blots as described above. Results from Northern blots showed that it hybridized only to the 1.4 kB mRNA and those from the Southern blots showed that it hybridzed only to a subset of the fragments that hybridized to plasmid pDS1. These results confirmed that the pDS1 contained an independent CDNA clone unlinked in the genome to the stearoyl-ACP desaturase gene. Since three of the four other stearoyl-ACP desaturase sequences are colinear with SEQ ID NO:1 up to its nucleotide position 1552 and since the initiation codon for the second open reading frame that encodes a polypeptide related to the yeast ribosomal protein is at nucleotides 1603 to 1605, one can deduce that in SEQ ID NO:1 the stearoyl-ACP cDNA ends somewhere between nucleotides 1552 and 1605, most likely at position 1552. Thus, while the entire cDNA insert in pDS1 may be used to alter fatty acid desaturation by overexpression or inhibition by antisense or co-suppression, the preferred sequence would be from nucleotide 1 to nucleotide 1552 in Seq ID NO:1.

Authentic soybean stearoyl-ACP desaturase clones that lack the apparently extraneous 3' non-coding region of pDS1 may be readily isolated by using the CDNA insert in pDS1 or SEQ ID NO:4 as a hybridization probe to screen soybean seed CDNA library and identifying the authentic cDNAs by sequence determination.

Mature soybean somatic embryo has several morphological and biochemical characteristics of maturing soybean seeds that make it a useful and rapid test model to study seed expression of foreign genes. Applicants expressed SEQ ID NO:1 in an antisense orientation with respect to a constitutive 35S (Cauliflower mosaic virus) promoter in somatic soybean embryos. Transformed mature soybean somatic embryos showed up to two-fold increase in the level of stearic acid. The level of expression varied significantly between embryos. This may be due to the embryos not being clonal. Analyses of a larger number of embryos is expected to increase the chance of finding transformants with even higher levels of 18:0.

The effect of overexpression of soybean mature stearoyl-ACP desaturase in somatic soybean embryos was studied by introducing a 35S-giladin promoter/sense mature stearoyl-ACP desaturase chimeric gene. While the fatty acid profile of the immature transgenic somatic embryos was normal, that of mature ones showed up to ten-fold increase in 18:0 level compared to untransformed embryos. Only about 20% of the transgenic embryos have the same profile as the normal embryos (less than 5% 18:0). The 18:0 levels in the remaining embryos varied from 5% to over 30%. The highest 18:0 level found in these transgenic embryos mimics the highest 18:0 level found in a soybean high-stearate mutant, A6. However, unlike soybean mutant A6, where almost all of the increase in 18:0 comes from 18:1, in the high 18:0 transgenic soybean mutants, the increase comes almost all from 18:2. This finding was repeated in another transformation experiment using somatic embryos from two other soybean lines, elite lines A2872 and A3015. Mature transgenic embryos from these lines also showed varying levels of increased 18:0. Similar range of 18:0 levels are reported for transgenic rapeseed plants transformed with rapeseed stearoyl-ACP desaturase in an antisense orientation [Knutzon et al. (1992) Proc. Natl. Acad. Sci. 89:2624–2628]. The ratio of 18:0/18:1+18:2+18:3 in these transformed lines ranges from 1.4 to 5.6 times that in the control embryos. Mature embryos from line G286/6/3 and G286/6/8 were germinated and the seeds from the transgenic plants will be analyzed for fatty acid composition. The over-expression of the mature form unexpectedly gave increased 18:0. Such inhibition of expression of the endogenous and foreign homologous genes has been observed in other plant tissues and has been termed "co-suppression". Applicants have observed co-suppression in other experiments with soybean somatic transformation. The co-suppression observed may be related to the large number of foreign gene copies introduced by the method used here. It has been suggested that co-suppression involves the same mechanism as antisense inhibition. Thus, the high stearic acid phenotype, even though exerted via co-suppression, demonstrates that SEQ ID NO:1 can effect anti-sense-like phenotype. If overexpression of the mature enzyme in the cytoplasm does reduce the level of 18:0, it may be masked either by the embryo to embryo variation in fatty acid composition or by the phenomenon of co-suppression. Analyses of seeds in transgenic soybean plants resulting from these experiments and/or transformation of soybean plants by another method that does not show high frequency of co-suppression will help resolve that question.

As expected, comparison of the deduced amino-acid sequences for soybean stearoyl-ACP desaturase and the rat microsomal stearoyl-CoA desaturases did not reveal any significant homology.

In vitro recombinant DNA techniques were used to make two fusion proteins:

a) a recombinant plasmid pGEXB that encodes a ca. 66 kD fusion protein consisting of a 28 kD glutathione-S-transferase (GST) protein fused at its C-terminus to the ca. 38 kD desaturase precursor protein at amino acid residue −10 from the N-terminus of the mature enzyme (Arg, +1) (SEQ ID NO:1). Extracts of E. coli cells harboring pGEXB, grown under conditions that induce the synthesis of the fusion protein, show stearoyl-ACP desaturase activity and expression of a ca. 66 kD fusion protein that cross-reacts with antibody made against soybean stearoyl-ACP desaturase and that binds to glutathione-agarose affinity column. The affinity column can be used to purify the fusion protein to near-homogeneity in a single step. The desaturase moiety can be cleaved off in the presence of thrombin and separated from the GST by re-chromatography on the glutathione-agarose column; and b) a recombinant plasmid, pNS2, that encodes a ca. 42 kD fusion protein consisting of 4 kD of the N-terminus of G-galactosidase fused at its C-terminus to the amino acid residue at position +10 (Ile) from the N-terminus of the mature desaturase protein (Arg, +1) (SEQ ID NO:1). Extract of E. coli cells harboring pNS2 express a ca. 42 kD protein that cross-reacts with antibody made against soybean stearoyl-ACP desaturase and show stearoyl-ACP desaturase activity.

E. coli (pGEXB) can be used to purify the stearoyl-ACP desaturase for use in structure-function studies on the enzyme, in immobilized cells or in extracellular desaturations [see Ratledge et al. (1984) Eds., Biotechnology for the Oils and Fats Industry, American Oil Chemists'Society]. E. coli (pNS2) can be used to express the desaturase enzyme in vivo. However, for in vivo function it may be necessary to introduce an electron donor, such as ferredoxin and NADPH:ferredoxin reductase. The ferredoxin gene has been cloned from a higher plant [Smeekens et al. (1985) Nucleic Acids Res. 13:3179–3194] and human ferredoxin has been expressed in E. coli [Coghlan et al. (1989) Proc. Natl. Acad. Sci. USA, 86:835–839]. Alternatively, one skilled in the art can express the mature protein in microorganisms using other expression vectors described in the art [Sambrook et al. (1989) Molecular Cloning: A Laboratory Manual, 2nd Ed. Cold Spring Harbor Laboratory Press; Milman (1987) Meth. Enzymol. 153:482–491; Duffaud et al. (1987) Meth. Enzymol. 153:492–507; Weinstock (1987) Meth. Enzymol. 154:156–163; E.P.O. Publication 0 295 959 A2).

The fragment of the instant invention may be used, if desired, to isolate related stearoyl-ACP desaturase cDNAs and genes, including those from plant species other than soybean. Isolation of related genes is well-known in the art. Southern blot analysis reveals that the soybean cDNA for the enzyme hybridizes to several, different-sized DNA fragments in the genomic DNA of tomato, rapeseed (*Brassica napus*), soybean, corn (a monocotyledenous plant) and Arabidopsis (which has a very simple genome). The Southern blot of corn DNA reveals that the soybean cDNA can also hybridize non-specifically, which may make the isolation of the corn gene more difficult. Although we do not know how many different genes or "pseudogenes" (non-functional genes) are present in any plant, it is expected to be more than one, since stearoyl-ACP desaturase is an important enzyme. Moreover, plants that are amphidiploid (that is, derived from two progenitor species), such as soybean, rapeseed (*B. nanus*), and tobacco will have genes from both progenitor species.

The nucleic acid fragment of the instant invention encoding soybean seed stearoyl-ACP desaturase cDNA, or a coding sequence derived from other cDNAs or genes for the enzyme, with suitable regulatory sequences, can be used to overexpress the enzyme in transgenic soybean as well as other transgenic species. Such a recombinant DNA construct may include either the native stearoyl-ACP desaturase gene or a chimeric gene. One skilled in the art can isolate the coding sequences from the fragment of the invention by using and/or creating sites for restriction endonucleases, as described in Sambrook et al. [(1989) Molecular Cloning: A Laboratory Manual, 2nd Ed. Cold Spring Harbor Laboratory Press]. Of particular utility are sites for Nco I (5'-CCATGG-3') and Sph I (5'-GCATGC-3') that allow precise removal of coding sequences starting with the initiating codon ATG. The fragment of the invention has a Nco I recognition sequence at nucleotide positions 1601–1606 (SEQ ID NO:1) that is 357 bp after the termination codon for the coding sequence. For isolating the coding sequence of stearoyl-ACP desaturase precursor from the fragment of the invention, an Nco I site can be engineered by substituting nucleotide A at position 69 with C. This will allow isolation of the 1533 bp Nco I fragment containing the precursor coding sequence. The expression of the mature enzyme in the cytoplasm is expected to desaturate stearoyl-CoA to oleoyl-CoA. For this it may be necessary to also express the mature ferredoxin in the cytoplasm, the gene for which has been cloned from plants [Smeekens et al. (1985) Nucleic Acids Res. 13:3179–3194]. For isolating the coding sequence for the mature protein, a restriction site can be engineered near nucleotide position 164. For example, substituting nucleotide G with nucleotide C at position 149 or position 154 would result in the creation of Nco I site or Sph I site, respectively. This will allow isolation of a 1453 bp Nco I fragment or a 1448 bp Sph I-Nco I fragment, each containing the mature protein sequence. Based on fusion protein studies, the N-terminus of the mature stearoyl-ACP desaturase enzyme is not critical for enzyme activity.

Antisense RNA has been used to inhibit plant target genes in a dominant and tissue-specific manner [see van der Krol et al. (1988) Gene 72:45–50; Ecker et al. (1986) Proc. Natl. Acad. Sci. USA 83:5372–5376; van der Krol et al. (1988) Nature 336:866–869; Smith et al. (1988) Nature 334:724–726; Sheehy et al. (1988) Proc. Natl. Acad. Sci. USA 85:8805–8809; Rothstein et al. (1987) Proc. Natl. Acad. Sci. USA 84:8439–8443; Cornelissen et al. (1988) Nucl. Acids Res. 17:833–843; Cornelissen (1989) Nucl. Acid Res. 17:7203–7209; Robert et al. (1989) Plant Mol. Biol. 13:399–409].

The use of antisense inhibition of the seed enzyme would require isolation of the coding sequence for genes that are expressed in the target tissue of the target plant. Thus, it will be more useful to use the fragment of the invention to screen seed-specific cDNA libraries, rather than genomic libraries or cDNA libraries from other tissues, from the appropriate plant for such sequences. Moreover, since there may be more than one gene encoding seed stearoyl-ACP desaturase, it may be useful to isolate the coding sequences from the other genes from the appropriate crop. The genes that are most highly expressed are the best targets for antisense inhibition. The level of transcription of different genes can be studied by known techniques, such as run-off transcription.

For expressing antisense RNA in soybean seed from the fragment of the invention, the entire fragment of the invention (that is, the entire cDNA for soybean stearoyl-ACP desaturase from nucleotides 1 to 1552, SEQ ID NO:1) may be used. There is evidence that the 3' non-coding sequences can play an important role in antisense inhibition [Ch'ng et al.(1989) Proc. Natl. Acad. Sci. USA 86:10006–10010]. There have also been examples of using the entire cDNA sequence for antisense inhibition [Sheehy et al. (1988) Proc. Natl. Acad. Sci. USA 89:8439–8443]. The NcoI and Eco RI sites can be modified to facilitate insertion of the sequences into suitable regulatory sequences in order to express the antisense RNA. The phenomenon of cosuppression has also been used to inhibit plant target genes in a tissue-specific manner. Cosuppression of an endogenous gene using the entire cDNA sequence (Napoli et al., The Plant Cell (1990) 2:279–289; van der Krol et al., The Plant Cell (1990) 2:291–299) as well as a partial cDNA sequence (730 bp of a 1770 bp CDNA) (Smith et al., Mol. Gen. Genetics (1990) 224:477–481) are known.

The nucleic acid fragments of the instant invention encoding stearoyl-ACP desaturase, or parts thereof, with suitable regulatory sequences, can be used to reduce the level of that desaturase, thereby altering fatty acid composition, in transgenic plants which contain an endogenous gene substantially homologous to the introduced nucleic acid fragment. The experimental procedures necessary for this are similar to those described above for the overexpression of the fatty acid desaturase nucleic acid fragments except that one may also use a partial cDNA sequence. For example, cosuppression of stearoyl-ACP desaturase in soybean resulting in altered levels of stearic fatty acid may be achieved by expressing in the sense orientation the entire or partial seed stearoyl-ACP desaturase cDNA found in pDS1 or PDS1S.

A preferred host soybean plant for the antisense RNA inhibition of stearoyl-ACP desaturase for producing a cocoa butter substitute in soybean seed oil is a soybean plant containing higher-than-normal levels of palmitic acid, such as A19 double mutant, which is being commercialized by Iowa State University Research Foundation, Inc. (315 Beardshear, Ames, Iowa 50011).

A preferred class of heterologous hosts for the expression of the coding sequence of stearoyl-ACP desaturase precursor or the antisense RNA are eukaryotic hosts, particularly the cells of higher plants. Particularly preferred among the higher plants are the oilcrops, such as soybean (*Glycine max*), rapeseed (*Brassica napus, B. campestris*), sunflower (*Helianthus annus*), cotton (*Gossypium hirsutum*), corn (*Zea mays*), cocoa (*Theobroma cacao*), and peanut (*Arachis hypogaea*). Expression in plants will use regulatory sequences functional in such plants.

The expression of foreign genes in plants is well-established [De Blaere et al.(1987) Meth. Enzymol. 153:277–291]. The origin of promoter chosen to drive the expression of the coding sequence or the antisense RNA is not critical as long as it has sufficient transcriptional activity to accomplish the invention by increasing or decreasing, respectively, the level of translatable mRNA for stearoyl-ACP desaturase in the desired host tissue. Preferred promoters include strong plant promoters (such as the constitutive promoters derived from Cauliflower Mosaic Virus that direct the expression of the 19S and 35S viral transcripts [Odell et al.(1985) Nature 313:810–812; Hull et al. (1987) Virology 86:482–493]), small subunit of ribulose 1,5-bisphosphate carboxylase [Morelli et al.(1985) Nature 315:200; Broglie et al.(1984) Science 224:838; Hererra-Estrella et al.(1984) Nature 310:115; Coruzzi et al.(1984) EMBO J. 3:1671; Faciotti et al.(1985) Bio/Technology 3:241], maize zein protein [Matzke et al. (1984) EMBO J. 3:1525], and chlorophyll a/b binding protein [Lampa et al.(1986) Nature 316:750–752].

Depending upon the application, it may be desirable to select inducible promoters and/or tissue- or development-specific promoters. Such examples include the light-inducible promoters of the small subunit of ribulose 1,5-bisphosphate carboxylase genes (if the expression is desired in tissues with photosynthetic function).

Particularly preferred tissue-specific promoters are those that allow seed-specific expression. This may be especially useful, since seeds are the primary source of vegetable oils and also since seed-specific expression will avoid any potential deleterious effect in non-seed tissues. Examples of seed-specific promoters include but are not limited to the promoters of seed storage proteins, which can represent up to 90% of total seed protein in many plants. The seed storage proteins are strictly regulated, being expressed almost exclusively in seeds in a highly tissue-specific and stage-specific manner [Higgins et al. (1984) Ann. Rev. Plant Physiol. 35:191–221; Goldberg et al. (1989) Cell 56:149–160]. Moreover, different seed storage proteins may be expressed at different stages of seed development.

Expression of seed-specific genes has been studied in great detail [see reviews by Goldberg et al. (1989) Cell 56:149–160 and Higgins et al. (1984) Ann. Rev. Plant Physiol. 35:191–221]. There are currently numerous examples for seed-specific expression of seed storage protein genes in transgenic dicotyledonous plants. These include genes from dicotyledonous plants for bean β-phaseolin [Sengupta-Gopalan et al. (1985) Proc. Natl. Acad. Sci. USA 82:3320–3324; Hoffman et al. (1988) Plant Mol. Biol. 11:717–729], bean lectin [Voelker et al. (1987) EMBO J. 6: 3571–3577], soybean lectin [Okamuro et al. (1986) Proc. Natl. Acad. Sci. USA 83:8240–8244], soybean kunitz trypsin inhibitor [Perez-Grau et al. (1989) Plant Cell 1:095–1109], soybean β-conglycinin [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123], pea vicilin [Higgins et al. (1988) Plant Mol. Biol. 11:683–695], pea convicilin [Newbigin et al. (1990) Planta 180:461], pea legumin [Shirsat et al. (1989) Mol. Gen. Genetics 215:326]; rapeseed napin [Radke et al. (1988) Theor. Appl. Genet. 75:685–694] as well as genes from monocotyledonous plants such as for maize 15-kD zein [Hoffman et al. (1987) EMBO J. 6:3213–3221], and barley β-hordein [Marris et al. (1988) Plant Mol. Biol. 10:359–366] and wheat glutenin [Colot et al. (1987) EMBO J. 6:3559–3564]. Moreover, promoters of seed-specific genes operably linked to heterologous coding sequences in chimeric gene constructs also maintain their temporal and spatial expression pattern in transgenic plants. Such examples include Arabidopsis thaliana 2S seed storage protein gene promoter to express enkephalin peptides in Arabidopsis and B. napus seeds [Vandekerckhove et al. (1989) Bio/Technology 7:929–932], bean lectin and bean β-phaseolin promoters to express luciferase [Riggs et al. (1989) Plant Sci. 63:47–57], and wheat glutenin promoters to express chloramphenicol acetyl transferase [Colot et al. (1987) EMBO J. 6:3559–3564].

Of particular use in the expression of the nucleic acid fragment of the invention will be the heterologous promoters from several extensively-characterized soybean seed storage protein genes such as those for the Kunitz trypsin inhibitor [Jofuku et al. (1989) Plant Cell 1:1079–1093; Perez-Grau et al. (1989) Plant Cell 1:1095–1109], glycinin [Nielson et al. (1989) Plant Cell 1:313–328], β-conglycinin [Harada et al. (1989) Plant Cell 1:415–425]. Promoters of genes for α- and β-subunits of soybean β-conglycinin storage protein will be particularly useful in expressing the mRNA or the antisense RNA to stearoyl-ACP desaturase in the cotyledons at mid- to late-stages of seed development [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123] in transgenic plants, since: a) there is very little position effect on their expression in transgenic seeds, and b) the two promoters show different temporal regulation: the promoter for the α-subunit gene is expressed a few days before that for the β-subunit gene; this is important for transforming rapeseed where oil biosynthesis begins about a week before seed storage protein synthesis [Murphy et al. (1989) J. Plant Physiol. 135:63–69].

Also of particular use will be promoters of genes expressed during early embryogenesis and oil biosynthesis. The native regulatory sequences, including the native promoter, of the stearoyl-ACP desaturase gene expressing the nucleic acid fragment of the invention can be used following its isolation by those skilled in the art. Heterologous promoters from other genes involved in seed oil biosynthesis, such as those for B. napus isocitrate lyase and malate synthase [Comai et al. (1989) Plant Cell 1:293–300], Arabidopsis ACP [Post-Beittenmiller et al. (1989) Nucl. Acids Res. 17:1777], B. napus ACP [Safford et al. (1988) Eur. J. Biochem. 174:287–295], B. campestris ACP [Rose et al. (1987) Nucl. Acids Res. 15:7197] may also be used. The partial protein sequences for the relatively-abundant enoyl-ACP reductase and acetyl-CoA carboxylase are published [Slabas et al. (1987) Biochim. Biophys. Acta 877:271–280; Cottingham et al. (1988) Biochim. Biophys. Acta 954: 201–207] and one skilled in the art can use these sequences to isolate the corresponding seed genes with their promoters.

Proper level of expression of stearoyl-ACP mRNA or antisense RNA may require the use of different chimeric genes utilizing different promoters. Such chimeric genes can be transferred into host plants either together in a single expression vector or sequentially using more than one vector.

It is envisioned that the introduction of enhancers or enhancer-like elements into either the native stearoyl-ACP desaturase promoter or into other promoter constructs will also provide increased levels of primary transcription for antisense RNA or in RNA for stearoyl-ACP desaturase to accomplish the inventions. This would include viral enhancers such as that found in the 35S promoter [Odell et al. (1988) Plant Mol. Biol. 10:263–272], enhancers from the opine genes (Fromm et al. (1989) Plant Cell 1:977–984), or enhancers from any other source that result in increased transcription when placed into a promoter operably linked to the nucleic acid fragment of the invention.

Of particular importance is the DNA sequence element isolated from the gene for the α-subunit of β-conglycinin that can confer 40-fold seed-specific enhancement to a constitutive promoter [Chen et al. (1988) EMBO J. 7:297–302; Chen et al. (1989) Dev. Genet. 10:112–122]. One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

The invention can also be accomplished by a variety of other methods to obtain the desired end. In one form, the invention is based on modifying plants to produce increased levels of stearoyl-ACP desaturase by virtue of having significantly larger numbers of copies of either the wild-type or a stearoyl-ACP desaturase gene from a different soybean tissue in the plants. This may result in sufficient increases in stearoyl-ACP desaturase levels to accomplish the invention.

Any 3' non-coding region capable of providing a polyadenylation signal and other regulatory sequences that may be required for the proper expression of the stearoyl-ACP desaturase coding region can be used to accomplish the invention. This would include the native 3' end of the substantially homologous soybean stearoyl-ACP desaturase gene(s), the 3' end from a heterologous stearoyl-ACP desaturase gene, the 3' end from viral genes such as the 3' end of the 35S or the 19S cauliflower mosaic virus transcripts, the 3' end from the opine synthesis genes, the 3' ends of ribulose 1,5 bisphosphate carboxylase or chlorophyll a/b binding protein, or 3' end sequences from any source such that the sequence employed provides the necessary regulatory information within its nucleic acid sequence to result in the proper expression of the promoter/stearoyl-ACP desaturase coding region combination to which it is operably linked. There are numerous examples in the art that teach the usefulness of different 3' non-coding regions.

Various methods of transforming cells of higher plants according to the present invention are available to those skilled in the art (see EPO publications 0 295 959 A2 and 0 318 341 A1). Such methods include those based on transformation vectors based on the Ti and Ri plasmids of Agrobacterium spp. It is particularly preferred to use the binary type of these vectors. Ti-derived vectors transform a wide variety of higher plants, including monocotyledonous and dicotyledonous plants, such as soybean, cotton and rape [Pacciotti et al.(1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178; Potrykus (1985) Mol. Gen. Genet. 199:183]. Other transformation methods are available to those skilled in the art, such as direct uptake of foreign DNA constructs [see EPO publication 0 295 959 A2], techniques of electroporation [see Fromm et al. (1986) Nature (London) 319:791] or high-velocity ballistic bombardment with metal particles coated with the nucleic acid constructs [see Kline et al. (1987) Nature (London) 327:70]. Once transformed the cells can be regenerated by those skilled in the art.

Of particular relevance are the recently described methods to transform foreign genes into commercially important crops, such as rapeseed [see De Block et al. (1989) Plant Physiol. 91:694–701], sunflower [Everett et al. (1987) Bio/Technology 5:1201], and soybean [McCabe et al. (1988) Bio/Technology 6:923; Hinchee et al. (1988) Bio/Technology 6:915; Chee et al. (1989) Plant Physiol. 91:1212–1218; Christou et al. (1989) Proc. Natl. Acad. Sci USA 86:7500–7504; EPO Publication 0 301 749 A2].

The use of restriction fragment length polymorphism (RFLP) markers in plant breeding has been well-documented in the art [see Tanksley et al. (1989) Bio/Technology 7:257–264). The nucleic acid fragment of the invention has been mapped to four different loci on a soybean RFLP map [Tingey et al. (1990) J. Cell Biochem., Supplement 14E p. 291, abstract R153]. It can thus be used as a RFLP marker for traits linked to these mapped loci. More preferably these traits will include altered levels of stearic acid. The nucleic acid fragment of the invention can also be used to isolate the stearoyl-ACP desaturase gene from variant (including mutant) soybeans with altered stearic acid levels. Sequencing of these genes will reveal nucleotide differences from the normal gene that cause the variation. Short oligonucleotides designed around these differences may be used as hybridization probes to follow the variation in stearic and oleic acids. Oligonucleotides based on differences that are linked to the variation may be used as molecular markers in breeding these variant oil traits.

SEQ ID NO:1 includes the nucleotide sequence of a soybean seed stearoyl-ACP desaturase cDNA and the translation reading frame that includes the open reading frame for the soybean seed stearoyl-ACP desaturase. The nucleotide sequence reads from 5' to 3'. Three letter codes for amino acids are used as defined by the Commissioner, 1114 OG 29 (May 15, 1990) incorporated by reference herein. Nucleotide 1 is the first nucleotide of the cDNA insert after the EcoRI cloning site of the vector and nucleotide 2243 is the last nucleotide of the cDNA insert of plasmid pDSI. Nucleotides 70 to 72 are the putative translation initiation codon, nucleotides 166 to 168 are the codon for the N-terminal amino acid of the purified enzyme, nucleotides 1243 to 1245 are the termination codon, nucleotides 1 to 69 are the 5' untranslated sequence, and nucleotides 1246 to at least 1552 are 3' untranslated sequence. Nucleotides 1603 to 2243 possibly represent a separate and unrelated cDNA sequence. SEQ ID NO:2 represents the partial sequence of a different soybean seed stearoyl-ACP desaturase cDNA. The first and last nucleotides (1 and 216 on clone 5) are read 5' to 3' and represent the 3' non-coding sequence. SEQ ID NO:3 represents the N-terminal sequence of the purified soybean seed stearoyl-ACP desaturase. SEQ ID NO:4 represents the degenerate coding sequence for amino acids 5 through 16 of SEQ ID NO:3. SEQ ID NO:5 represents a complementary mixture of degenerate oligonucleotides to SEQ ID NO:4.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Applicants have deposited *Escherichia coli* strain XL-1 Blue, DS1, plasmid pDSI, under terms of the Budapest Treaty for purposes of patent procedure, with American Type Culture Collection (ATCC), 1239 Parklawn Drive, Rockville, Md. 10852, U.S.A.

This plasmid has been designated as ATCC 68331, and is referred to throughout this application as pDSI.

EXAMPLE 1

ISOLATION OF cDNA FOR SOYBEAN SEED STEAROYL-ACP DESATURASE PREPARATION OF [9,10-$^3$H]-STEAROYL-ACP

Purification of Acyl Carrier Protein (ACP) from *E. coli*

To frozen *E. coli* cell paste, (0.5 kg of ½ log phase growth of *E. coli* B grown on minimal media and obtained from Grain Processing Corp, Muscatine, Iowa) was added 50 mL of a solution 1M in Tris, 1M in glycine, and 0.25M in EDTA. Ten mL of 1M $MgCl_2$ was added and the suspension was thawed in a water bath at 50° C. As the suspension approached 37° C. it was transferred to a 37° C. bath, made to 10 mM in 2-mercaptoethanol and 20 mg of DNAse and 50 mg of lysozyme were added. The suspension was stirred for 2 h, then sheared by three 20 second bursts in a Waring Blendor. The volume was adjusted to 1 L and the mixture was centrifuged at 24,000×g for 30 min. The resultant supernatant was centrifuged at 90,000×g for 2 h. The resultant high-speed pellet was saved for extraction of acyl-ACP synthase (see below) and the supernatant was adjusted to pH 6.1 by the addition of acetic acid. The extract was then made to 50% in 2-propanol by the slow addition of cold 2-propanol to the stirred solution at 0° C. The resulting precipitate was allowed to settle for 2 h and then removed by centrifugation at 16,000×g. The resultant supernatant was adjusted to pH 6.8 with KOH and applied at 2 mL/min to a 4.4×12 cm column of DEAE-Sephacel which had been equilibrated in 10 mM MES, pH 6.8. The column was washed with 10 mM MES, pH 6.8 and eluted with 1 L of a gradient of LiCl from 0 to 1.7M in the same buffer. Twenty mL fractions were collected and the location of eluted by ACP determined by applying 10 gL of every second fraction to a lane of a native polyacrylamide (20% acrylamide) gel electro-phoresis (PAGE). Fractions eluting at about 0.7M LiCl contained nearly pure ACP and were combined, dialyzed overnight against water and then lyophilized.

Purification of Acyl-ACP Synthase

Membrane pellets resulting from the high-speed centrifugation described above were homogenized in 380 mL of 50 mM Tris-Cl, pH 8.0, and 0.5M in NaCl and then centrifuged at 80,000×g for 90 min. The resultant supernatant was discarded and the pellets resuspended in 50 mM Tris-Cl, pH 8.0, to a protein concentration of 12 mg/mL. The membrane suspension was made to 2% in Triton X-100 and 10 mM in $MgCl_2$, and stirred at 0° C. for 20 min before centrifugation at 80,000×g for 90 min. The protein in the resultant supernatant was diluted to 5 mg/mL with 2% Triton X-100 in 50 mM Tris-Cl, pH 8.0 and, then, made to 5 mM ATP by the addition of solid ATP (disodium salt) along with an equimolar amount of $NaHCO_3$. The solution was warmed in a 55° C. bath until the internal temperature reached 53° C. and was then maintained at between 53° C. and 55° C. for 5 min. After 5 min the solution was rapidly cooled on ice and centrifuged at 15,000×g for 15 min. The supernatant from the heat treatment step was loaded directly onto a column of 7 mL Blue Sepharose 4B which had been equilibrated in 50 mM Tris-Cl, pH 8.0, and 2% Triton X-100. The column was washed with 5 volumes of the loading buffer, then 5 volumes of 0.6M NaCl in the same buffer and the activity was eluted with 0.5M KSCN in the same buffer. Active fractions were assayed for the synthesis of acyl-ACP, as described below, combined, and bound to 3 mL settled-volume of hydroxylapatite equilibrated in 50 mM Tris-Cl, pH 8.0, 2% Triton X-100. The hydroxylapatite was collected by centrifugation, washed twice with 20 mL of 50 mM Tris-Cl, pH 8.0, 2% Triton X-100. The activity was eluted with two 5 mL washes of 0.5M potassium phosphate, pH 7.5, 2% Triton X-100. The first wash contained 66% of the activity and it was concentrated with a 30 kD membrane filtration concentrator (Amicon) to 1.5 mL.

Synthesis of [9,10-$^3$H]-Stearoyl-ACP

A solution of stearic acid in methanol (1 mM, 34.8 µL) was mixed with a solution of [9,10-$^3$H]stearate (Amersham) containing 31.6 µCi of $^3$H and dried in a glass vial. The ACP preparation described above (1.15 mL, 32 nmoles) was added along with 0.1 mL of 0.1M ATP, 0.05 mL of 80 mM DTT, 0.1 mL of 8M LiCl, and 0.2 mL of 13% Triton X-100 in 0.5M Tris-Cl, pH 8.0, with 0.1M $MgCl_2$. The reaction was mixed thoroughly and 0.3 mL of the acyl-ACP synthase preparation was added. After 1 h at 37° C., a 10 µL aliquot was taken and dried on a small filter paper disc. The disc was washed extensively with chloroform:methanol:acetic acid (8:2:1, v:v:v) and radioactivity retained on the disc was taken as a measure of stearoyl-ACP. At 1 h about 67% of the ACP had been consumed and the reaction did not proceed further in the next 2 h. The reaction mix was diluted 1 to 4 with 20 mM Tris-Cl, pH 8.0, and applied to a 1 mL DEAE-Sephacel column equilibrated in the same buffer. The column was washed in sequence with 5 mL of 20 mM Tris-Cl, pH 8.0, 5 mL of 80% 2-propanol in 20 mM Tris-Cl, pH 8.0, and eluted with 0.5M LiCl in 20 mM Tris-Cl, pH 8.0. The column eluate was passed directly onto a 3 mL column of octyl-sepharose CL-4B which was washed with 10 mL of 20 mM potassium phosphate, pH 6.8, and then eluted with 35% 2-propanol in 2 mM potassium phosphate, pH 6.8. The eluted volume (5.8 mL) contained 14.27 µCi of $^3$H (49% yield based on ACP). The eluted product was lyophilized and redissolved at a concentration of 24 µM [$^3$H]stearoyl-ACP at 0.9 mCi/µmole.

PREPARATION OF ALKYL-ACP AFFINITY COLUMN Synthesis of N-hexadecyliodoacetamide

1-Hexadecylamine (3.67 mmole) was dissolved in 14.8 mL of $CH_2Cl_2$, cooled to 4° C., and 2.83 mmoles of iodoacetic anhydride in 11.3 mL of $CH_2Cl_2$ was added dropwise to the stirred solution. The solution was warmed to room temperature and held for 2 h. The reaction mixture was diluted to about 50 mL with $CH_2Cl_2$ and washed 3 times (25 mL) with saturated sodium bicarbonate solution and then 2 times with water. The volume of the solution was reduced to about 5 mL under vacuum and passed through 25 mL of silica in diethyl ether. The eluate was reduced to an off-white powder under vacuum. This yielded 820 mg (2.03 mmoles) of the N-hexadecyliodoacetamide (71.8% yield). The 300MHz $^1$H NMR spectra of the product was consistent with the expected structure.

Synthesis of N-Hexadecylacetamido-S-ACP

E. coli ACP prepared as above (10 mg in 2 mL of 50 mM Tris-Cl, pH 7.6) was treated at 37° C. with 50 mM DTT for 2 h. The solution was made to 10% TCA, held at 0° C. for 20 min and centrifuged to pellet. The resultant pellet was washed (2×2 mL) with 0.1M citrate, pH 4.2 and redissolved in 3 mL of 50 mM potassium phosphate buffer. The pH of the ACP solution was adjusted to 7.5 with 1M KOH and 3 mL of N-hexadecyliodoacetamide (3 mM in 2-propanol) was added. A slight precipitate of the N-hexadecyliodoacetamide was redissolved by warming the reaction mix to 45° C. The mixture was held at 45° C. for 6 h. SDS-PAGE on 20% acrylamide PAGE gel showed approximately 80% conversion to an ACP species of intermediate mobility between the starting, reduced ACP and authentic palmitoyl-ACP. Excess N-hexadecyliodoacetamide was removed from the reaction mix by 4 extractions (3-mL) with $CH_2Cl_2$ with gentle mixing to avoid precipitation of the protein at the interface.

Coupling of N-Hexadecylacetamido-S-ACP to CNBr-activated Sepharose 4B

Cyanogen bromide-activated Sepharose 4B (Pharmacia, 2 g) was suspended in 1 mM HCl and extensively washed by filtration and resuspension in 1 mM HCl and finally one wash in 0.1M NaHCO$_3$, pH 8.3. The N-hexadecyl-acetamido-S-ACP prepared above was diluted with an equal volume of 0.2M NaHCO$_3$, pH 8.3. The filtered cyanogen bromide-activated Sepharose 4B (about 5 mL) was added to the N-hexadecylacetamido-S-ACP solution, the mixture was made to a volume of 10 mL with the 0.1M NaHCO$_3$, pH 8.3, and mixed by tumbling at room temperature for 6 h. Protein remaining in solution (Bradford assay) indicated approximately 85% binding. The gel suspension was collected by centrifugation, washed once with the 0.1M NaHCO$_3$, pH 8.3, and resuspended in 0.1M ethanolamine adjusted to pH 8.5 with HCl. The suspension was allowed to stand at 4° C. overnight and then washed by centrifugation and re-suspension in 12 mL of 0.1M acetate, pH 4.0, 0.5M in NaCl and then 0.1M NaHCO$_3$, pH 8.3, 0.5M in NaCl. The alkyl-ACP Sepharose 4B was packed into a 1×5.5 cm column and washed extensively with 20 mM bis-tris propane-Cl (BTP Cl), pH 7.2, before use.

STEAROYL-ACP DESATURASE ASSAY

Stearoyl-ACP desaturase was assayed as described by McKeon et al. [(1982) J. Biol. Chem. 257:12141–12147] except for using [9,10-$^3$H]-stearoyl-ACP. Use of the tritiated substrate allowed assaying the enzyme activity by release of tritium as water, although the assay based on the tritium release underestimates desaturation by a factor of approximately 4 relative to that observed using $^{14}$C-stearoyl-ACP by the method of McKeon et al. [(1982) J. Biol. Chem 257:12141–12147], apparently because not all tritium is at carbons 9 and 10. Nevertheless, this modification makes the enzyme assay more sensitive, faster and more reliable. The reaction mix consisted of enzyme in 25 µL of 230 µg/mL bovine serum albumin (Sigma), 49 µg/mL catalase (Sigma), 0.75 mM NADPH, 7.25 µM spinach ferredoxin, and 0.35 µM spinach ferredoxin:NADPH$^+$ oxidoreductase, 50 mM Pipes, pH 6.0, and 1 µM [9,10-$^3$H]-stearoyl-ACP (0.9 mCi/µmole). All reagents, except for the Pipes buffer, labeled substrate and enzyme extract, were preincubated in a volume of 7.25 µL at pH 8.0 at room temperature for 10 min before adding 12.75 µL the Pipes buffer and labeled substrate stocks. The desaturase reaction was usually terminated after 5 min by the addition of 400 µL 10% trichloroacetic acid and 50 µL of 10 mg/mL bovine serum albumin. After 5 min on ice, the protein precipitate was removed by centrifugation at 13,000×g for 5 min. An aliquot of 425 µL was removed from the resultant supernatant and extracted twice with 2 mL of hexane. An aliquot of 375 µL of the aqueous phase following the second hexane extraction was added to 5 mL of Scinti-Verse® Bio HP (Fisher) scintillation fluid and used to determine radioactivity released as tritium.

PURIFICATION OF SOYBEAN SEED STEAROYL-ACP DESATURASE

Developing soybean seeds, ca. 20–25 days after flowering, were harvested and stored at −80° C. until use. 300 g of the seeds were resuspended in 600 mL of 50 mM BTP-Cl, pH 7.2, and 5 mM dithiothreitol (DTT) in a Waring Blendor. The seeds were allowed to thaw for a few minutes at room temperature to 4° C. and all of the purification steps were carried out at 4° C. unless otherwise noted. The seeds were homogenized in the blendor three times for 30 s each and the homogenate was centrifuged at 14,000×g for 20 min. The resultant supernatant was centrifuged at 100,000×g for 1 h. The resultant high-speed supernatant was applied, at a flow-rate of 5 mL/min to a 2.5×20 cm Blue Sepharose column equilibrated in 10 mM BTP-Cl, pH 7.2, 0.5 mM DTT. Following a wash with 2 column volumes of 10 mM BTP-Cl, pH 7.2, 0.5 mM DTT, the bound proteins were eluted in the same buffer containing 1M NaCl. The eluting protein peak, which was detected by absorbance at 280 nm, was collected and precipitated with 80% ammonium sulfate. Following collection of the precipitate by centrifugation at 10,000×g for 20 min, its resuspension in 10 mM potassium phosphate, pH 7.2, 0.5 mM DTT, overnight dialysis in the same buffer precipitate, and clarification through a 0.45 micron filter, it was applied to a 10 mm×25 cm Widepores™ PEI (NH$_2$) anion-exchange column (Baker) at 3 mL/min thoroughly equilibrated in buffer A (10 mM potassium phosphate, pH 7.2). After washing the column in buffer A until no protein was eluted, the column was subjected to elution by a gradient from buffer A at 0 min to 0.25M potassium phosphate (pH 7.2) at 66 min at a flow rate of 3 mL/min. Three mL fractions were collected. The desaturase activity eluted in fractions 17–25 (the activity peak eluted at ca. 50 mM potassium phosphate). The pooled fractions were made to 60 mL with buffer A and applied at 1 mL/min to a 1×5.5 cm alkyl-ACP column equilibrated in buffer A containing 0.5 mM DTT. After washing the bound protein with the start buffer until no protein was eluted, the bound protein was eluted by a gradient from buffer A containing 0.5 mM DTT at 0 min to 0.5M potassium phosphate, pH 7.2, 0.5 mM DTT at 60 min and 1M potassium phosphate, pH 7.2, 0.5 mM DTT. Four mL fractions were collected. Fractions 15–23, which contained the enzyme with the highest specific activity, were pooled and concentrated to 3 mL by a 30 kD Centricon® concentrator (Millipore) and desalted in a small column of G-25 Sephadex® equilibrated with 25 mM bis-Tris-Cl, pH 6.7. The desalted sample was applied at 1 mL/min to a chromatofocussing Mono P HR 5/20 (Pharmacia) column equilibrated with 25 mM bis-Tris-Cl, pH 6.7, washed with a column volume of the same buffer, and eluted with 1:10 dilution of Polybuffer 74 (Pharmacia) made to pH 5.0 with HCl. Desaturase activity eluted in two peaks: one in fraction 30 corresponding to a pI of ca. 6.0 and the other in fraction 35, corresponding to a pI of ca. 5.7. The protein in the two peaks were essentially composed of ca. 38 kD polypeptide. The first peak had a higher enzyme specific activity and was used for further characterization as well as for further purification on reverse-phase chromatography.

Mono P fractions containing the first peak of enzyme activity were pooled and applied to a C$_4$ reverse-phase HPLC column (Vydac) equilibrated with buffer A (5% acetonitrile, 0.1% trifluoroacetic acid) and eluted at 0.1 mL/min with a gradient of 25% buffer B (100% acetonitrile, 0.1% trifluoroacetic acid) and 75% buffer A at 10 min to 50% buffer B and 50% buffer A at 72.5 min. A single major peak eluted at 41.5% buffer B that also ran as a ca. 38 kD protein based on SDS-PAGE. The protein in the peak fraction was used to determine the N-terminal amino acid sequence on a Applied Biosystems 470A Gas Phase Sequencer. The PTH amino acids were analysed on Applied Biosystems 120 PTH Amino Acid Analyzer.

The N-terminal sequence of the ca. 38 kD polypeptide was determined through 16 residues and is shown in SEQ ID NO:3.

CLONING OF SOYBEAN SEED STEAROYL-ACP DESATURASE cDNA

Based on the N-terminal amino acid sequence of the purified soybean seed stearoyl-ACP desaturase (SEQ ID NO:3), amino acids 5 through 16, which are represented by the degenerate coding sequence, SEQ ID NO:4, was chosen to design the complementary mixture of degenerate oligonucleotides (SEQ ID NO:5).

The design took into account the codon bias in representative soybean seed genes encoding Bowman-Birk protease inhibitor [Hammond et al. (1984) J. Biol. Chem. 259:9883–9890], glycinin subunit A-2B-1a (Utsumi et al. (1987) Agric. Biol. Chem. 51:3267–3273], lectin (1e-1) [Vodkin et al. (1983) Cell 34:1023–1031], and lipoxygenase-1 [Shibata et al. (1987) J. Biol. Chem. 262:10080–10085]. Five deoxyinosines were used at selected positions of ambiguity.

A cDNA library was made as follows: Soybean embryos (ca. 50 mg fresh weight each) were removed from the pods and frozen in liquid nitrogen. The frozen embryos were ground to a fine powder in the presence of liquid nitrogen and then extracted by Polytron homogenization and fractionated to enrich for total RNA by the method of Chirgwin et al. [Biochemistry (1979) 18:5294–5299]. The nucleic acid fraction was enriched for poly $A^+$ RNA by passing total RNA through an oligo-dT cellulose column and eluting the poly $A^+$ RNA by salt as described by Goodman et al. [(1979) Meth. Enzymol. 68:75–90]. cDNA was synthesized from the purified poly $A^+$ RNA using cDNA Synthesis System (Bethesda Research Laboratory) and the manufacturer's instructions. The resultant double-stranded DNA was methylated by DNA methylase (Promega) prior to filling-in its ends with T4 DNA polymerase (Bethesda Research Laboratory) and blunt-end ligating to phosphorylated Eco RI linkers using T4 DNA ligase (Pharmacia). The double-stranded DNA was digested with Eco RI enzyme, separated from excess linkers by passing through a gel filtration column (Sepharose CL-4B), and ligated to Lambda ZAP vector (Stratagene) as per manufacturer's instructions. Ligated DNA was packaged into phage using Gigapack packaging extract (Stratagene) according to manufacturer's instructions. The resultant cDNA library was amplified as per Stratagene's instructions and stored at −80° C.

Following the instructions in Lambda ZAP Cloning Kit Manual (Stratagene), the cDNA phage library was used to infect E. coli BB4 cells and plated to yield ca. 80,000 plaques per petri plate (150 mm diameter). Duplicate lifts of the plates were made onto nitrocellulose filters (Schleicher & Schuell). Duplicate lifts from five plates were prehybridized in 25 mL of Hybridization buffer consisting of 6×SSC (0.9M NaCl, 0.09M sodium citrate, pH 7.0), 5×Denhardt's [0.5 g Ficoll (Type 400, Pharmacia), 0.5 g polyvinylpyrrolidone, 0.5 g bovine serum albumin (Fraction V; Sigma)], 1 mM EDTA, 1% SDS, and 100 ug/mL denatured salmon sperm DNA (Sigma Chemical Co.) at 45° C. for 10 h. Ten pmol of the hybridization probe (see above) were end-labeled in a 52.5 uL reaction mixture containing 50 mM Tris-Cl, pH 7.5, 10 mM $MgCl_2$, 0.1 mM spermidine-HCl (pH 7.0), 1 mM EDTA (pH 7.0), 5 mM DDT, 200 uCi (66.7 pmoles) of gamma-labeled $AT^{32}P$ (New England Nuclear) and 25 units of T4 polynucleotide kinase (New England Biolabs). After incubation at 37° C. for 45 min, the reaction was terminated by heating at 68° C. for 10 min. Labeled probe was separated from unincorporated $AT^{32}P$ by passing the reaction through a Quick-Spine (G-25 Sephadex®) column (Boehringer Mannheim Biochemicals). The purified labeled probe ($1.2 \times 10^7$ dpm/pmole) was added to the prehybridized filters, following their transfer to 10 mL of fresh Hybridization buffer. Following incubation of the filters in the presence of the probe for 16 h in a shaker at 48° C., the filters were washed in 200 mL of Wash buffer (6×SSC, 0.1% SDS) five times for 5 min each at room temperature, and then once at 48° C. for 5 min. The washed filters were air dried and subjected to autoradiography on Kodak XAR-2 film in the presence of intensifying screens (Lightening Plus, DuPont Cronex®) at −80° C. overnight. Six positively-hybridizing plaques were subjected to plaque purification as described in Sambrook et al. [(1989) Molecular Cloning: A Laboratory Manual, 2nd ed., Cold Spring Harbor Laboratory Press]. Following the Lambda ZAP Cloning Kit Instruction Manual (Stratagene), sequences of the pBluescript vector, including the cDNA inserts, from each of six purified phages were excised in the presence of a helper phage and the resultant phagemids were used to infect E. coli XL-1 Blue cells resulting in double-stranded plasmids, pDS1 to pDS6. The restriction maps of all six plasmids, though not identical, showed a common 0.7 kb Bgl II fragment found in the desaturase gene (see below).

DNA from plasmids pDS1-pDS6 were made by the alkaline lysis miniprep procedure described in Sambrook et al. [(1989) Molecular Cloning: A Laboratory Manual, 2nd Ed. Cold Spring Harbor Laboratory Press]. The alkali-denatured double-stranded DNAs were sequenced using Sequenase® T7 DNA polymerase (US Biochemical Corp.) and the manufacturer's instructions. The sequence of the cDNA insert in plasmid pDS1 is shown in SEQ ID NO:1.

EXAMPLE 2

EXPRESSION OF SOYBEAN SEED STEAROYL-ACP DESATURASE IN E. coli
Construction of Glutathione-S-Transferase:
Stearoyl-ACP Desaturase Fusion Protein Plasmid pDS1 was linearized with Hind III enzyme, its ends filled-in with Klenow fragment (Bethesda Research Laboratory) in the presence of 50 μM each of all four deoxynucleotide triphosphates as per manufacturer's instructions, and extracted with phenol:chloroform (1:1). Phosphorylated Eco RI linkers (New England Biolabs) were ligated to the DNA using T4 DNA ligase (New England Biolabs). Following partial digestion with Bgl II enzyme and complete digestion with excess Eco RI enzyme, the DNA was run on an agarose gel and stained with ethidium bromide. The 2.1 kb DNA fragment resulting from a partial Bgl II and Eco RI digestion was cut out of the gel, purified using USBioclean™ (US Biochemicals), and ligated to Bam HI and Eco RI cleaved vector pGEX2T [Pharmacia; see Smith et al. (1988) Gene 67:31] using T4 DNA ligase (New England Biolabs). The ligated mixture of DNAs were used to transform E. coli XL-1 blue cells (Stratagene). Transformants were picked as ampicillin-resistant cells and the plasmid DNA from several transformants analyzed by digestion with Bam HI and Eco RI double restriction digest, as described by Sambrook et al. [(1989) Molecular Cloning: A Laboratory Manual, 2nd Ed. Cold Spring Harbor Laboratory Press]. Plasmid DNA from one transformant, called pGEXB, showed the restriction pattern expected from the correct fusion. The double-stranded plasmid pGEXB was purified and sequenced to confirm the correct fusion by the Sequenase kit (US Biochemical Corp.). The fusion protein consists of a 28 kD glutathione-S-transferase protein fused at its C-terminus to the desaturase precursor protein at Ser at residue −10 from the N-terminus of the mature enzyme (Arg, +1) (SEQ ID NO:1). Thus, it includes ten amino acids from the transit peptide sequence in addition to the mature protein.

Inducible Expression of the Glutathione-S-
Transferase-Stearoyl-ACP Desaturase Fusion
Protein Five mL precultures of plasmids pGEXB and pGEX2T, which were grown overnight at 37° C. in LB medium

[Sambrook et al. (1989) Molecular Cloning: A Laboratory Manual, 2nd Ed. Cold Spring Harbor Laboratory Press] containing 100 ug/mL ampicillin, were diluted 1:10 in fresh LB medium containing 100 µg/mL ampicillin and continued to grow on a shaker at 37° C. for another 90 min before adding isopropylthio-β-D-galactoside and ferric chloride to final concentrations of 0.3 mM and 50 µM, respectively. After an additional 3 h on a shaker at 37° C., the cultures were harvested by centrifugation at 4,000×g for 10 min at 4° C. The cells were resuspended in one-tenth of the culture volume of freshly-made and ice-cold Extraction buffer (20 mM sodium phosphate, pH 8.0, 150 mM NaCl, 5 mM EDTA and 0.2 mM phenylmethyl-sulfonyl fluoride) and re-centrifuged as above. The resultant cells were resuspended in 1/50 vol of the culture in Extraction buffer and sonicated for three ten-second bursts. The sonicated extracts were made to 1% in Triton X-100 and centrifuged at 8,000×g for 1 min in Eppendorf Micro Centrifuge (Brinkmann Instruments) to remove the cellular debris. The supernatant was poured into a fresh tube and used for enzyme assays, SDS-PAGE analysis and purification of the fusion protein.

Five µL aliquots of the extracts were assayed for stearoyl-ACP desaturase activity in a 1 min reaction, as described in Example 1. The activities [net pmol of stearoyl-ACP desaturated per min per mL of extract; the blank (no desaturase enzyme) activity was 15 pmol/min/ml] are shown below:

| Reaction mixture | Net pmol/min/mL |
| --- | --- |
| E. coli (pGEX2T) | 0 |
| E. coli (pGEXB) | 399 |
| E. coli (pGEXB) - NADPH | 0 |
| E. coli (pGEXB) - ferredoxin | 0 |
| E. coli (pGEXB) - ferredoxin-NADPH reductase | 3 |

These results show that the desaturase enzyme activity is present in the extract of E. coli cells containing pGEXB but not in that of cells containing the control plasmid pGEX2T. Furthermore, this activity was dependent on an exogenous electron donor.

Proteins in extracts of E. coli cells harboring plasmids pGEX2T or pGEXB were resolved by SDS-PAGE, transferred onto Immobilon®-P (Millipore) and cross-reacted with mouse antibody made against purified soybean stearoyl-ACP desaturase, as described by Sambrook et al. [(1989) Molecular Cloning: A Laboratory Manual, 2nd Ed. Cold Spring Harbor Laboratory Press]. The resultant Western blot showed that pGEXB encodes for ca. 64 kD GST-stearoyl-ACP desaturase fusion polypeptide, although some lower molecular-weight cross-reacting polypeptides can also be observed, which may represent either a degradation or incomplete synthesis of the fusion protein. It is not known whether the GST-desaturase fusion protein is enzymatically active, since the activity observed may be due to the incomplete fusion by the peptides seen here. The fusion polypeptide was not present in extracts of cells harboring the control plasmid (pGEX2T) nor in extracts of cells harboring pGEXB that were not induced by isopropylthio-β-D-galactoside Purification of the Glutathione-S-Transferase-Stearoyl-ACP Desaturase Fusion Protein The GST-desaturase fusion protein was purified in a one step glutathione-agarose affinity chromatography under non-denaturing conditions, following the procedure of Smith et al. [Gene (1988) 67:31]. For this, the bacterial cell extract was mixed with 1 mL glutathione-agarose (sulfur-linkage, Sigma), equilibrated with 20 mM sodium phosphate, pH 8.0, 150 mM NaCl, for 10 min at room temperature. The beads were collected by centrifugation at 1000×g for 1 min, and washed three times with 1 mL of 20 mM sodium phosphate, pH 8.0, 150 mM NaCl (each time the beads were collected by centrifugation as described above). The fusion protein was eluted with 5 mM reduced glutathione (Sigma) in 50 mM Tris-Cl, pH 8.0. The proteins in the eluted fraction were analyzed by SDS-PAGE and consisted of mostly pure ca. 64 kD GST-desaturase polypeptide, 28 kD GST and a trace of ca. 38 kD desaturase polypeptide. The fusion polypeptide was cleaved in the presence of thrombin, as described by Smith et al. [Gene (1988) 67:31].

Construction of β-Galactosidase-Stearoyl-ACP Desaturase Fusion Protein

Plasmid pDS1 DNA was digested with Ssp I and Pvu I enzymes and the digested DNA fragments were resolved by electrophoresis in agarose. The blunt-ended 2.3 kb Ssp I fragment was cut out of the agarose (Pvu I cleaves a contaminating 2.3 kb Ssp I fragment), purified by USBioclean™ (US Biochemical Corp.), and ligated to vector plasmid pBluescript SK (−) (Stratagene) that had previously been filled-in with Klenow fragment (Bethesda Research Laboratory) following linearization with Not I enzyme. The ligated DNAs were transformed into competent E. coli XL-1 blue cells. Plasmid DNA from several ampicillin-resistant transformants were analysed by restriction digestion. One plasmid, called pNS2, showed the expected physical map. This plasmid is expected to encode a ca. 42 kD fusion protein consisting of 4 kD N-terminal of β-galactosidase fused at its C-terminus to isoleucine at residue +10 from the N-terminus of the mature desaturase protein (Arg, +1) (SEQ ID NO:1). Thus, it includes all but the first 10 amino acids of the mature protein. Nucleotide sequencing has not been performed on pNS2 to confirm correct fusion.

Five mL of preculture of E. coli cells harboring plasmid pNS2 grown overnight in LB medium containing 100 µg/mL ampicillin was added to 50 mL of fresh LB medium with 100 µg/mL ampicillin. After additional 1 h of growth at 37° C. in a shaker, isopropylthio-β-D-galactoside and ferric chloride were added to final concentrations of 0.3 mM and 50 µM, respectively. After another 2 h on a shaker at 37° C., the culture was harvested by centrifugation at 4,000×g for 10 min at 4° C. The cells were resuspended in 1 mL of freshly-made and ice-cold TEP buffer (100 mM Tris-Cl, pH 7.5, 10 mM EDTA and 0.1 mM phenylmethylsulfonyl fluoride) and re-centrifuged as above. The cells were resuspended in 1 mL of TEP buffer and sonicated for three ten-second bursts. The sonicates were made to 1% in Triton X-100, allowed to stand in ice for 5 min, and centrifuged at 8,000×g for 1 min in an Eppendorf Micro Centrifuge (Brinkmann Instruments) to remove the cellular debris. The supernatant was poured into a fresh tube and used for enzyme assays and SDS-PAGE analysis.

A 1 µL aliquot of the extract of E. coli cells containing plasmid pNS2 was assayed for stearoyl-ACP desaturase activity in a 5 min reaction, as described above. The extract showed activity of 288 pmol of stearoyl-ACP desaturated per min per ml of the extract [The blank (no desaturase enzyme) activity was 15 pmol/min/mL].

Proteins in the extract of E. coli cells harboring plasmids pNS2 were resolved by SDS-PAGE, transferred onto Immobilon®-P (Millipore) and cross-reacted with mouse antibody made against purified soybean stearoyl-ACP desaturase, as described in Sambrook et al. [(1989) Molecular Cloning: A Laboratory Manual, 2nd Ed. Cold Spring Harbor Laboratory Press]. The resultant Western blot showed that pNS2 encodes for ca. 42 kD β-galactosidase-stearoyl-ACP desaturase fusion polypeptide.

EXAMPLE 3

Use Of Soybean Seed Stearoyl-ACP Desaturase Sequence In Plasmid pDSIS As A Restriction Fragment Length Polymorphism (RFLP) Marker Plasmid pDSIS was linearized by digestion with restriction enzyme Eco RI in standard conditions as described in Sambrook et al. ((1989) Molecular Cloning: A Laboratory Manual, 2nd Ed. Cold Spring Harbor Laboratory Press] and labeled with $^{32}$P using a Random Priming Kit from Bethesda Research Laboratories under conditions recommended by the manufacturer. The resulting radioactive probe was used to probe a Southern blot [Sambrook et al., (1989) Molecular Cloning: A Laboratory Manual, 2nd Ed. Cold Spring Harbor Laboratory Press] containing genomic DNA from soybean [*Glycine max* (cultivar Bonus) and *Glycine soja* (PI81762)], digested with one of several restriction enzymes. After hybridization and washes under standard conditions [Sambrook et al., (1989) Molecular Cloning: A Laboratory Manual, 2nd Ed. Cold Spring Harbor Laboratory Press] autoradiograms were obtained and different patterns of hybridization (polymorphisms) were identified in digests performed with restriction enzymes Bcl I and Eco RI. The same probe was then used to map the polymorphic pDS1 S loci on the soybean genome, essentially as described by Helentjaris et al. [(1986) Theor. Appl. Genet. 72:761–769]. Plasmid pDS1 S probe was applied, as described above, to Southern blots of Eco RI or Bcl I digested genomic DNAs isolated from 68 F2 progeny plants resulting from a *G. max* Bonus×*G. soja* PI81762 cross. The bands on the autoradiograms were interpreted as resulting from the inheritance of either paternal (Bonus) or maternal (PI81762) pattern, or both (a heterozygote). The resulting data were subjected to genetic analysis using the computer program Mapmaker [Lander et al., (1987) Genomics 1:174–181]. In conjunction with previously obtained data for 436 anonymous RFLP markers in soybean [Tingey et al. (1990) J. Cell. Biochem., Supplement 14E p. 291, abstract R153], we were able to position two genetic loci corresponding to the pDSIS probe on the soybean genetic map. The polymorphism linked to the Bcl I fragment maps to linkage group 18 (formerly called LG 29) 11.9 cM distal to marker 3513 and the polymorphism linked to the Eco RI fragment maps to linkage group 20 (formerly called LG 19) 62 cM distal to marker 2813 [Rafalski and Tingey (in press) in Genetic Maps (S. Obrein, Ed., 6th edition, Cold Spring Harbor Laboratory Press, Cols Spring Harbor, N.Y.]. This information will be useful in soybean breeding targeted towards developing lines with altered saturate levels, especially for the recessive high stearic acid mutant phenotypes, since these are most likely be due to loss of seed stearoyl-ACP desaturase enzyme.

EXAMPLE 5

Isolation Of The Preferred Sequence Encoding Soybean

Stearoyl-ACP Desaturase

Five ug of plasmid pDSI DNA was digested with Hind III (BRL) and NCO I (BRL) as per the manufacturer's instructions, its ends filled-in with Klenow enzyme and religated with T4 DNA ligase. The ligation mixture was used to transform *E. coli* cells and DNA from the ampicillin-resistant transformants analyzed by restriction digests. One plasmid, designated pDSIS, was confirmed to have deleted the most of the apparently extraneous sequence. To delete the approximately 55 additional bases between position 1552 and the filled-in Nco I site one skilled in the art can digest plasmid pDS1 S with one of the enzymes that cut in the multiple cloning sites of the vector at the 3' end of the cDNA, such as Cla I, and digest back with an exonuclease, such as Bal-31, to the desired position and reclone the shorter cDNA insert.

EXAMPLE 6

Expression of Soybean Stearoyl-ACP Desaturase cDNAs in Transgenic Soybean Somatic Embryos To test the biological effect of expressing SEQ ID NO:1 in the antisense orientation, the constitutive chimeric gene, 35S/antisense SEQ ID NO:1, was introduced into somatic soybean embryos by particle bombardment. The cassette for constitutive gene expression originated from pK35K which, in turn, is derived from PKNK. Plasmid PKNK is a pBR322-based vector containing a chimeric gene for plant kanamycin resistance: nopaline synthase (NOS) promoter/neomycin phosphotransferase (NPT) II coding region/3' NOS chimeric gene. Plasmid PKNK has been deposited with the ATCC and bears the deposit accession number 67284. A map of this plasmid is shown in Lin. et al., Plant Physiol. (1987) 84:856–861. The NOS promoter region is a 296 bp Sau 3A-Pst I fragment corresponding to nucleotides –263 to +33, with respect to the transcription start site, of the NOS gene described by Depicker et al. (1982) J. Appl. Genet. 1:561–574. The Pst I site at the 3' end was created at the translation initiation codon of the NOS gene. The NptII coding region is a 998 bp Hind III-Bam HI fragment obtained from transposon Tn5 (Beck et al., Gene (1982) 19:327–336) by the creation of Hind III and Bam HI sites at nucleotides 1540 and 2518, respectively. The 3' NOS is a 702 bp Bam HI-Cla I fragment from nucleotides 848 to 1550 of the 3' end of the NOS gene (Depicker et al., J. Appl. Genet. (1982) 1:561–574) including its' polyadenylation region. pKNK was converted to pK35K by replacing its Eco RI-Hind III fragment containing the NOS promoter with a Eco RI-Hind III fragment containing the CaMV 35S promoter. The Eco RI-Hind III 35S promoter fragment is the same as that contained in pUC35K that has been deposited with the ATCC and bears the deposit accession number 67285. The 35S promoter fragment was prepared as follows, and as described in Odell et al., Nature (1985) 313:810–813, except that the 3' end of the fragment includes CaMV sequences to +21 with respect to the transcription start site. A 1.15 KB Bgl II segment of the CaMV genome containing the region between –941 and +208 relative to the 35S transcription start site was cloned in the Bam HI site of the plasmid pUC13. This plasmid was linearized at the Sal I site in the polylinker located 3' to the CaMV fragment and the 3' end of the fragment was shortened by digestion with nuclease Bal31. Following the addition of Hind III linkers, the plasmid DNA was recircularized. From nucleotide sequence analysis of the isolated clones, a 3' deletion fragment was selected with the Hind III linker positioned at +21. The 35S promoter fragment was isolated as an Eco RI-Hind III fragment, the Eco RI site coming from the polylinker of pUC13.

The NPTII coding region in plasmid pK35K was removed from plasmid pK35K by digestion with Hind III and Bam HI restriction enzymes. Following digestion, the ends of the DNA molecules were filled-in using Klenow enzyme. Xba I linkers (New England Biolabs) were then ligated on the ends and the plasmid was recircularized to form plamsid pK35X, which lacked the NPT II coding region. Plasmid pDS1 was digested with restriction endonucleases Eco RI and Hind III, then the ends of the DNA molecules were filled-in using Klenow enzyme after which Xba I linkers (New England Biolabs) were added using T4 DNA ligase. The 2.3 kB fragment containing SEQ ID NO:1, now containing Xho I sites at either end, was gel isolated and cloned into the plasmid pK35X at its unique Xba I site to result in plasmid pX3 that had SEQ ID NO:1 cloned in the antisense orientation with respect to the promoter. The orientation of the cDNA relative to the promotors was established by digestion with appropriate restriction endonucleases.

For a plant selectable marker, a 3.2 kB Sal I restriction fragment containing a chimeric plant hygromycin resistance gene was used. It comprises a chimeric sequence of 35S promoter of CaMV genome of isolate Cabb-JI/chlorophyl a/b binding protein 5' leader sequence, bacterial hygromycin B phosphotransferase (HPT) coding region/3' region of nopaline synthase (NOS) gene. The 35S promoter/Cab leader is on a 1.4 kB Sal I—Nco I fragment that is derived from a 1.4 kB Eco RI—Nco I fragment [Harpster et. al. (1988) Mol. Gen. Genet. 212:182–190] by replacing the EcoRI site with multiple cloning sites (Sal I/Xba I/Bam HI, with the Sal I being the distal site) . The HPT coding sequence (GenBank Accession no K01193) is on a ca. 1 kB Nco I—Kpn I fragment that was derived by PCR using a 31-mer sense primer made to positions 211–233 that had additional nucleotides for Bsp HI recognition sequence at its 5' end and a 36-mer antisense primer made to positions 1216–1236 that had additional nucleotides for Kpn I recognition sequence at its 5' end. The 3' NOS sequence is derived from the 702 bp Bam HI-Cla I fragment (see description above) by replacing the Bam HI and Cla I sites with those of Kpn I and Sal I, respectively. The 3.2 kB Sal I fragment was cloned into the Sal I site of plasmid pX3 to result in plasmid pHX3. Plasmid pHX3 was used in transformation of soybean somatic embryos.

To test the effect of expressing the mature stearoyl-ACP desaturase in soybean somatic embryos, a chimeric sequence of seed-specific gliadin promoter/sense mature stearoyl-ACP desaturase/3' gliadin gene was constructed. For this, plasmid pEN3a was the starting point.

Plasmid pEN3a is a pBR322-derived vector that contains a 1.9 kB seed-specific expression cassette. This cassette comprises of a 935 bp Hind III - Nco I fragment with a modified wheat gliadin promoter [Summer-Smith et. al. (1985) Nucleic Acids Res. 13:3905–3916] ligated to a 1 kB Nco I - Eco RV fragment with the 3' end of gliadin gene. The promoter fragment was modified in three ways: a) it was digested with restriction enzyme Nsi at position 212 and filled-in with Klenow, then a 338 bp Acc I - Hga I fragment containing sequences between positions −392 and −55 with respect to the transcription start site of the 35S promoter [Odell et. al. (1988) Plant Molecular Biol. 10:263–272], which contains a plant enhancer element, was gel purified, its ends filled-in with Klenow, and ligated in the forward orientation into the filled-in Nsi site, b) the Nco I site at position 480 was destroyed by Nco I digestion followed by Klenow fill-in, and religation, and c) the promoter region was made by PCR using a 31-mer sense primer made to positions 1–31 and a 34-mer antisense primer made to positions 564–597 (positions 594–596 being the translation initiation codon), except that a C was used instead of a T at the 5' end, that resulted in a Nco I site at the position of the initiation codon. This resulted in a ca 935 bp Hind III - Nco I fragment containing the gliadin promoter with the enhancer element. The 3' end of the gliadin gene was isolated as a 1 kB fragment starting from the Nco I site at position 1509 to the EcoRV site at position 1610 and it contains the polyadenylation signal.

Nco I site was introduced at the codon for the first amino acid of the mature stearoyl-ACP desaturase enzyme as follows: plasmid pDS1 was digested with restriction enzyme Ssp I and ligated to a 33-mer sense and 29 antisense primers made to positions 165–192 in SEQ ID NO:1. The sense primer included 6 additional bases (5' -CATGGC ... ) at it's 5' end including the 4 bp Nco I site overhang and the antisense primer included 2 additional bases ( ... GC-3' ) at the 3' end. Following ligation the DNA was digested with Nco I. The resultant 1.44 kB Nco I fragment, containing the coding region of the mature stearoyl-ACP desaturase and 358 bp of 3' non-coding sequence, was gel purified and ligated into the Nco I site in plasmid pEN3a. The resultant plasmid, pDE9, was cleaved with Hind III and ligated to a 3.2 kB Hind III fragment containing the 35S promoter/ hygromycin resistance coding region/3'NOS, as described above. The flanking Hind III sites were derived by cloning the 3.2 kB Sal I fragment described above into the Sal I site of vector pUC1813 [Kay and McPherson (1987) Nucleic Acids Res. 15:2778] that is flanked by Hind III sites. The resultant plasmid, pHE9 was used to transform cultured soybean somatic embryos.

Transformation Of Somatic Soybean Embryo Cultures

Soybean embryogenic suspension cultures are maintained in 35 mL liquid media (SB55) on a rotary shaker, 150 rpm, at 28° C. with mixed fluorescent and incandescent lights on a 16:8 h day/night schedule. Cultures were subcultured every four weeks by inoculating approximately 35 mg of tissue into 35 mL of liquid medium.

Soybean (cultivar fayette) embryogenic suspension cultures were transformed with pHE9 or pHX3 by the method of particle gun bombardment (see Kline et al. (1987) Nature (London) 327:70). A Du Pont Biolistic PDS1000/HE instrument (helium retrofit) was used for these transformations.

To 50 uL of a 60 mg/mL 1 mm gold particle suspension was added (in order); 5 µL DNA(1 µg/µL), 50 µl $CaCl_2$ (2.5M), and 20 µL spermidine (0.1M). The particle preparation was agitated for 3 min, spun in a microfuge for 10 sec and the supernatant removed. The DNA-coated particles were then washed once in 400 µL 70% ethanol and resuspended in 40 µL of anhydrous ethanol. The DNA/particle suspension was sonicated three times for 1 sec each. Five FL of the DNA-coated gold particles were then loaded on each macro carrier disk.

Approximately 500–700 mg of a four week old suspension culture was placed in an empty 60×15 mm petri dish and the residual liquid removed from the tissue with a pipette. For each transformation experiment, approximately 5–10 plates of tissue were normally bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Seven to ten days post bombardment, the liquid media was exchanged with fresh SB55 containing 50 mg/L hygromycin. The selective media was refreshed weekly. Seven weeks post bombardment, green, transformed tissue was observed growing from untransformed, necrotic embryogenic clusters. Isolated green tissue was removed and inoculated into individual flasks to generate clonal, transgenic embryogenic suspension culture line. Thus, each new line was treated as an independent transformation event. These suspensions can then either be maintained as suspensions of transgenic embryos clustered in an immature developmental stage through subculture or induced to develop into mature embryos by transfer onto a solid agar medium (SB103) containing no hormones or antibiotics. Embryos were cultured for eight weeks at 26° C. with mixed fluorescent and incandescent lights on a 16:8 h day/night schedule. During this period, individual embryos were removed from the clusters and analyzed at various stages of embryo development. After eight weeks, the developmentally mature embryos become suitable for germination. Individual embryos can be regenerated into whole plants following germination.

TABLE

Media:

SB55 Stock Solutions (g/L):

MS Sulfate 100X Stock

| | |
|---|---|
| MgSO$_4$ 7H2O | 37.0 |
| MnSO$_4$ H2O | 1.69 |
| ZnSO$_4$ 7H2O | 0.86 |
| CuSO$_4$ 5H2O | 0.0025 |

MS Halides 100X Stock

| | |
|---|---|
| CaCl$_2$ 2H$_2$O | 44.0 |
| KI | 0.083 |
| CoCl$_2$ 6H$_2$O | 0.00125 |
| KH$_2$PO$_4$ | 17.0 |
| H$_3$BO$_3$ | 0.62 |
| Na$_2$MoO$_4$ 2H$_2$O | 0.025 |

MS FeEDTA 100X Stock

| | |
|---|---|
| Na$_2$EDTA | 3.724 |
| FeSO$_4$ 7H$_2$O | 2.784 |

B5 Vitimin Stock 10 g m-inositol
100 mg nicotinic acid
100 mg pyridoxine HCl
1 g thiamine SB55 (per Liter)

10 mL each MS stocks
1 mL B5 Vitaimin stock
0.8 g NH$_4$NO$_3$
3.033 g KNO$_3$
1 mL 2,4-D (10 mg/mL stock)
60 g sucrose
0.667 g asparagine
pH 5.7

SB103 (per Liter)

MS Salts
6% maltose
750 mg MgCl$_2$
0.2% Gelrite
pH 5.7

Analysis Of Transgenic Mature Soybean Somatic Embryos

Mature soybean somatic embryos can serve as a model system to test soybean seed trait expression. The immature somatic soybean embryos, while in the globular embryo stage in liquid culture, contain very low amounts of triacylglycerol (oil) or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominant seed proteins (a' subunit of b-conglycinin, Kunitz Trypsin Inhibitor III and Soybean Seed Lectin) are essentially absent. Upon transfer to hormone free media to allow differentiation to the maturing somatic embryo state as described above, triacylglycerol becomes the most abundant lipid class. As well, mRNAs for a' -subunit of b-conglycinin, Kunitz Trypsin Inhibitor III and Soybean Seed Lectin become very abundant messages in the total mRNA population. In these respects the somatic soybean embryo system behaves very similarly to maturing zygotic soybean embryos in vivo, and is therefore a good and rapid model system for analyzing the phenotypic effects of modifying the expression of genes in the fatty acid biosynthesis pathway. Similar somatic embryo culture systems have been documented and used in another oilseed crop, rapeseed (Taylor et al. (1990) Planta 181:18–26). Fatty acid analysis of single embryos was determined either by direct trans-esterification of individual seeds in 0.5 mL of methanolic H$_2$SO$_4$ (2.5%) or by hexane extraction of bulk seed samples followed by trans-esterification of an aliquot in 0.8 mL of 1% sodium methoxide in methanol. Fatty acid methyl esters were extracted from the methanolic solutions into hexane after the addition of an equal volume of water. The results of this analysis are shown in Tables A–D.

The effect of 35S:antisense stearoyl-ACP desaturase in individual mature embryos from different transgenic lines, derived by transformation of fayette line with pHX3, is shown in Table A. Relative to the untransformed fayette line, the average 18:0 levels in transgenic embryos is up 39%. In embryos of some lines the 18:0 level is increased up to 2-fold.

TABLE A

Percent Fatty Acids in Transgenic Soybean Cultured Embryos Transformed with 35S:Antisense Stearoyl-ACP Desaturase

| Transgenic Embryo # | 16:0 | 18:0 | 18:1 | 18:2 | 18:3 | 18:0 as % control |
|---|---|---|---|---|---|---|
| 1 | 17 | 3.0 | 12.9 | 49 | 15 | 93 |
| 2 | 13 | 4.6 | 13.8 | 54 | 12 | 143 |
| 3 | 17 | 3.4 | 10.2 | 49 | 17 | 106 |
| 4 | 12 | 3.1 | 10.9 | 57 | 14 | 97 |
| 5 | 16 | 6.7 | 12.7 | 48 | 14 | 209 |
| 6 | 12 | 4.9 | 15.1 | 46 | 14 | 154 |
| 7 | 17 | 4.8 | 15.1 | 46 | 14 | 151 |
| 8 | 15 | 3.2 | 10.7 | 52 | 15 | 99 |
| 9 | 15 | 6.5 | 15.5 | 46 | 13 | 203 |
| Transgenic Average | 15 | 4.5 | 13.1 | 51 | 14 | 139 |
| Control 1 | 14 | 3.0 | 15.7 | 52. | 12 | 95 |
| Control 2 | 18 | 3.3 | 4.7 | 50 | 17 | 102 |
| Control 3 | 16 | 3.3 | 4.6 | 53 | 16 | 103 |
| Control Average | 16 | 3.2 | 8.3 | 52 | 15 | 100 |

Plasmid pHE9, carrying 35S-gliadin promoter/sense mature stearoyl-ACP desaturase chimeric gene was transformed into somatic embryogenic suspension cultures of soybean line fayette. The percent fatty acids in individual mature embryos from one transgenic line, designated G204, is shown in Table B. Relative to the untransformed fayette embryos, the average 18:0 levels in transgenic embryos of line G204 is up almost 3-fold. However, in some individual embryos of this line the 18:0 level is increased upto 10-fold.

TABLE B

Percent Fatty Acids In Transgenic Soybean Cultured Embryos Transformed with GP/Sense Stearoyl-ACP Desaturase (Experiment I)

| Transgenic Embryo # | 16:0 | 18:0 | 18:1 | 18:2 | 18:3 | 18:0 as % control |
|---|---|---|---|---|---|---|
| 1 | 17 | 14.4 | 7.2 | 44 | 18 | 447 |
| 2 | 16 | 3.6 | 11.3 | 57 | 12 | 112 |
| 3 | 17 | 11.7 | 6.0 | 52 | 14 | 362 |
| 4 | 15 | 29.2 | 5.9 | 33 | 17 | 906 |
| 5 | 17 | 4.1 | 12.2 | 52 | 15 | 128 |
| 6 | 15 | 2.8 | 6.7 | 59 | 16 | 86 |
| 7 | 16 | 3.3 | 8.8 | 55 | 17 | 102 |
| 8 | 18 | 4.0 | 8.8 | 55 | 14 | 125 |
| Transgenic Average | 16 | 9.1 | 8.4 | 51 | 15 | 283 |
| Control 1 | 19 | 3.4 | 9.3 | 51 | 18 | 106 |
| Control 2 | 18 | 2.8 | 11.7 | 54 | 13 | 88 |
| Control 3 | 18 | 3.1 | 8.8 | 53 | 17 | 95 |
| Control 4 | 19 | 3.3 | 9.3 | 50 | 18 | 103 |
| Control 5 | 17 | 3.5 | 11.3 | 52 | 16 | 107 |
| Control 6 | 18 | 3.3 | 11.9 | 57 | 13 | 101 |
| Average | 18 | 3.2 | 10.4 | 53 | 16 | 100 |

To better understand the range of 18:0 levels in transgenic line G204, the percent fatty acid in extracts of another 59 individual embryos of the untransformed (control) line and another 100 individual embryos of the transformed line G204 was determined by gas chromatography (Table C). While all 59 untransformed embryo have less than 5% 18:0, only 20 out of 100 of the transformed embryos had less than 5% 18:0. The 18:0 levels in the remaining embryos varied from 5% to over 30%. The highest 18:0 level found in these transgenic embryos mimics the highest 18:0 level found in a soybean high-stearate mutant, A6. However, unlike soybean mutant a6 where almost all of the increase in 18:0 comes from 18:1, in the high 18:0 transgenic soybean mutants, the increase comes almost all from 18:2.

TABLE C

Frequency Distribution of Stearic Acid Levels in Transgenic Soybean Cultured Embryos Transformed with GP:Sense Stearoyl-ACP Desaturate (Experiment I)

| % 18:0 | No. of Individuals in Untransformed Controls | No. of Individuals in Transformed Embryos |
|---|---|---|
| 0.0–5.0 | 59 | 20 |
| 5.0–7.5 | 0 | 9 |
| 7.5–10.0 | 0 | 13 |
| 10.0–12.5 | 0 | 17 |
| 12.5–15.0 | 0 | 12 |
| 15.0–20.0 | 0 | 8 |
| 20.0–22.5 | 0 | 10 |
| 22.5–25.0 | 0 | 4 |
| 25.0–27.5 | 0 | 4 |
| 27.5–30.0 | 0 | 1 |
| 30.0–32.5 | 0 | 2 |

In another transformation, experiments plasmid pHE9 was introduced into somatic embryos from two other soybean lines, elite lines A2872 and A3015, as described above. Mature transgenic embryos from transformed line G286/11/1 (from line A3015), G286/6/8 (from A2872 line), G286/6/3 (from A2872 line), and control embryos were analysed for fatty acid composition determined. The average percent fatty acids of several different embryos from each of these lines is shown in Table D.

TABLE D

Percent Fatty Acids in Transgenic Soybean Cultured Embryos Transformed with GP:Sense Stearoyl-ACP Desaturase (Experiment II)

| Line | Number of Embryos | 16:0 | 18:0 | 18:1 | 18:2 | 18:3 | 20 + 22 |
|---|---|---|---|---|---|---|---|
| Control | 21 | 13.6 | 3.3 | 14.8 | 54.3 | 13.9 | 0 |
| G286/11/1 | 12 | 13.1 | 4.5 | 18.3 | 49.7 | 14.3 | 0 |
| G286/6/8 | 8 | 14.8 | 5.2 | 16.7 | 51.6 | 11.1 | 0 |
| G286/6/3 | 8 | 13.2 | 15.6 | 10.0 | 44.8 | 14.5 | 2 |

The ratio of 18:0/18:1+18:2+18:3 in transformed lines ranges from 1.4 to 5.6 times that in the control embryos. Mature embryos from line G286/6/3 and G286/6/8 were germinated and the seeds from the transgenic plants will be analyzed for fatty acid composition.

EXAMPLE 7

Isolation of a Soybean Stearoyl-ACP Desaturase Gene From a High-Stearic Acid Mutant Soybean Line Total RNA was isolated from immature seeds of high-stearic acid mutant soybean line A356 and the wildtype (WT) parent line following the method described by Verwoerd,et al., (Nucleic Acids Research (1989) Volume 17 Number 6). Poly A+ RNA was isolated from total RNA by employing the PolyATract system (Promega). Approximately 50 ng of poly A+ RNA or 3 ug of total RNA from mutant and wild-type soybean lines were subject to RT-PCR as described by the enzyme supplier (Perkin Elmer Cetus), using the following primers:

| RB61 | 5'-ACTTCGCGGCCGCATGGCTTCCACCCTCCG-3' SEQ ID NO: 8 |
| RB62 | 5'-CTTCGCGGCCGCTTAGAGTAGTACTTCCCT-3' SEQ ID NO: 9. |

These primers were designed to anneal to the coding region of the cDNA insert in plasmid pDS1. The RB61 PCR primer embraces the starting methionine codon of the mature peptide, and inserts an in-frame Not I restriction site upstream in order to aid subcloning. The RB62 PCR primer was designed embraces the stop codon of the peptide, as well as an in-frame Not I restriction site downstream in order to aid subcloning. The amplification portion of the RT-PCR reaction was carried out as follows:

1 cycle at 95° C. for 2 minutes;

3 cycles at 95° C. for 1 minute, 50° C. for 1 minute, 65° C. for 1 minute 30 seconds;

30 cycles at 95° C. for 1 minute, 60° C. for 1 minute, and 72° C. for 1 minute 30 seconds;

1 cycle at 72° C. for 7 min.;

Amplified DNA was held at 4° C. The expected 1120 bp fragment was recovered. The identity of the PCR products as encoding soybean stearoyl-ACP desaturase was confirmed by restriction enzyme mapping using enzymes known to digest the pDS1 cDNA insert. The 1120 bp PCR products were then digested with Not I restriction enzyme. The released Not I fragment encoding soybean stearoyl-ACP desaturase purified and subcloned into the Not I site of the protein expression vector pGEX-4T3 (Pharmacia). Orientation of the inserts in the resulting clones was analyzed by PCR. Clone pRB13 contained the coding region for stearoyl-ACP desaturase from A356 in the correct orientation relative to transcription. Proteins encoded by inserts isolated from A356, pWT, and the pDS1 plasmid clones were expressed and purified employing the Pharmacia standard Glutathione S-transferase protocol (Pharmacia). Expressed proteins were analyzed by SDS-PAGE, and assayed for stearoyl-ACP desaturase enzymatic activity. Initial assays demonstrated enzymatic activity for the pDS1 clone, and no activity in the A356 putative mutant clone. Clones containing the WT stearoyl-ACP desaturase gene and the A356-derived putative mutant stearoyl-ACP desaturase gene were sequenced and compared to the known soybean stearoyl-ACP desaturase gene sequence (SEQ ID NO:1). The A356 clone pRB13 was approximately 95% homologous at the nucleotide level with the pDS1 coding region; however this gene appeared to be an isozyme or second stearoyl-ACP desaturase gene. This second type of stearoyl-ACP desaturase gene was called pDS2. Amino acid homology between the pDS1 enzyme and the mutant pDS2 enzyme was 99%. Amino acid 43 of the mutant enzyme was changed from a lysine to a glutamine residue by the substitution of a G for A nucleotide. This region of the enzyme is known to be highly conserved in other known stearoyl-ACP desaturases; however, no others sequenced stearoyl-ACP desaturases share this substitution.

The identified mutation can be exploited by using the PCR- or RFLP-based molecular markers described above for detection of high stearic acid germplasm by detection of this mutation. This information can then be used to direct the breeding of this trait by analysis of the progeny of crosses of soybean plants harboring the mutant stearoyl-ACP desaturase gene into elite lines or into other interesting genetically altered germplasm. This detection method would allow breeders to rapidly identify plants that contain the desired mutation directly cross this generation of plants, thus eliminating the need to wait until for analysis of seed in order to make selections for subsequent breeding. This technique would eliminate one generation from each breeding cycle, significantly shortening the timelines for breeding this desireable trait into other genetic backgrounds.

In order to test the fidelity of this identification method, the following PCR primers were prepared:

| RB100 | 5'-CCAGAAGATTGAGATTTTCA-3' | SEQ ID NO: 10 |
|---|---|---|
| RB101 | 5'-CCAGAAGATTGAGATTTTCG-3' | SEQ ID NO: 11 |
| RB92 | 5'-GCCAACTTTATATCGCCG-3' | SEQ ID NO: 12. |

RB100 represents a portion of the WT (i.e., non-mutant) stearoyl-ACP desaturase gene sequence, whereas RB101 represents the corresponding portion of the mutant (pDS2) sequence comprising the identified mutation. PCR was performed according to the manufacturer's instruction (Perkin Elmer GeneAmp PCR Reagent Kit) using 100 pmol of RB100 or RB101 as forward primers and 100 pmol of the RB92 as the reverse primer. The following thermocycling conditions were employed:

1 cycle at 96° C. for 2 minutes;

20 cycles at 95° C. for 1 minute, 59° C. for 1 minute, and 72° C. for 1 minute 30 seconds;

1 cycle at 72° C. for 7 minutes;

Amplified DNAs were chilled to 4° C. Template DNAs consisted of 10 ng of plasmid DNAs harboring WT and pDS2 inserts encoding the wild-type (WT) and mutant (pDS2) stearoyl-ACP desaturases. Analysis of the resulting PCR products demonstrated that, under the employed conditions, use of the RB100 forward primer yielded the expected fragment only in the presence of WT template DNA; no fragment was detected when the template DNA was derived from pDS2. As expected, the RB101 forward primer yielded the expected fragment only in the presence of template DNA encoding the mutant enzyme. Similar PCR reactions could be performed on DNA extracts from plants in order to determine whether the mutation is present.

The nucleotide substitution of the mutant gene created new Nsp V, Taq I, Hinf I, and Tfi I restriction enzyme sites. These and any other enzymes that recognize the sequence spanning the mutated region (TGAGATTTTC(A or G)AATCTTTGGA) could be used as diagnostic RFLP molecular markers. Identification of test plants possessing the described mutation is accomplished by comparing Southern blots of test plants with digested DNAs from mutant or wildtype germplasm, and observing diagnostic changes in restriction fragment lengths following probing with the stearoyl-ACP desaturase gene or a portion thereof.

What is claimed is:

1. A nucleic acid fragment comprising a nucleotide sequence encoding the soybean seed stearoyl-ACP desaturase cDNA corresponding to the nucleotides 1 to 1552 in SEQ ID NO:1, or any nucleic acid fragment substantially homologous therewith that encodes a stearoyl-ACP desaturase sequence thereto.

2. A nucleic acid fragment comprising a nucleotide sequence encoding the soybean seed stearoyl-ACP desaturase CDNA corresponding to the nucleotides 1 to 1552 in SEQ ID NO:1, or any soybean stearoyl-ACP desaturase gene or cDNA substantially homologous thereto.

3. A chimeric gene capable of transforming a soybean plant cell comprising a nucleic acid fragment of claim 1 operably linked to suitable regulatory sequences producing altered levels of stearic acid in the plant cell wherein the nucleic acid fragment of claim 1 is operably linked, in antisense orientation, to suitable regulatory sequences producing altered levels of steric acid in the plant cell.

4. A chimeric gene capable of transforming a plant cell or an oil-producing species comprising a nucleic acid fragment, comprising a nucleotide sequence encoding the soybean seed stearoyl-ACP desaturase cDNA corresponding to the nucleotides 70-1245 in SEQ ID NO:1, or any nucleic acid fragment substantially similar thereto, that encodes a stearoyl-ACP desaturase sequence thereto, operably linked, in a sense or antisense orientation, to suitable regulatory sequences resulting in altered levels of stearic acid in the plant cell.

5. A chimeric gene capable of transforming a plant cell or an oil-producing species comprising a nucleic acid fragment, comprising a nucleotide sequence encoding the soybean seed stearoyl-ACP desaturase cDNA corresponding to the nucleotides 166 to 1245 in SEQ ID NO:1, operably linked, in a sense or antisense orientation, to suitable regulatory sequences resulting in altered levels of stearic acid in the plant cell.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2243 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Glycine max (B) STRAIN: Cultivar Wye
(D) DEVELOPMENTAL STAGE: Developing seeds (vii) IMMEDIATE SOURCE:
(A) LIBRARY: cDNA to mRNA
(B) CLONE: pDS1

(ix) FEATURE:
(A) NAME/KEY: 5'non-coding sequence
(B) LOCATION: 1..69
(D) OTHER INFORMATION: /note= "IDENTIFICATION METHOD=Deduced by proximity to location 70-72"

(ix) FEATURE:
(A) NAME/KEY: Putative translation initiation codon
(B) LOCATION: 70..72
(D) OTHER INFORMATION: /note= "IDENTIFICATION METHOD=Similarity of the context of the methionine codon in the open reading frame to translation (ix) FEATURE:
(A) NAME/KEY: Putative transit peptide coding sequence
(B) LOCATION: 70..165
(D) OTHER INFORMATION: /note= "IDENTIFICATION METHOD=Deduced by proximity to location 70-72 and location 166-1242"

(ix) FEATURE:
(A) NAME/KEY: Mature protein coding sequence
(B) LOCATION: 166..1242
(D) OTHER INFORMATION: /note= "IDENTIFICATION METHOD=Experimental determination of N-terminal amino acid sequence and subunit size of purified soybean (ix) FEATURE:
(A) NAME/KEY: Translation termination codon
(B) LOCATION: 1243..1245
(D) OTHER INFORMATION: /note= "IDENTIFICATION METHOD=The translation codon ends the open reading frame for a protein of the expected size"

(ix) FEATURE:
(A) NAME/KEY: 3'non-coding sequence
(B) LOCATION: 1246..2243
(D) OTHER INFORMATION: /note= "IDENTIFICATION METHOD=Established by proximity to location 1243-1245"

(xi) SEQUENCE DESCRIPTION: SEQ ID NO:1:

```
CTTCTACATT ACTCTCTCTT CTCCTAAAAA TTTCTAATGC TTCCATTGCT TCATCTGACT      60
CACTCATCAA TGGCTCTGAG ACTGAACCCT ATCCCCACCC AAACCTTCTC CCTCCCCCAA     120
ATGCCCAGCC TCAGATCTCC CCGCTTCCGC ATGGCTTCCA CCCTCCGCTC CGGTTCCAAA     180
GAGGTTGAAA ATATTAAGAA GCCATTCACT CCTCCCAGAG AAGTGCATGT TCAAGTAACC     240
CACTCTATGC CTCCCCAGAA GATTGAGATT TTCAAATCTT TGGAGGATTG GGCTGACCAG     300
AACATCTTGA CTCATCTTAA ACCTGTAGAA AAATGTTGGC AACCACAGGA TTTTTTACCC     360
GACCCCTCCT CAGATGGATT TGAAGAGCAA GTGAAGGAAC TGAGAGAGAG AGCAAAGGAG     420
ATTCCAGATG ATTACTTTGT TGTTCTTGTC GGAGACATGA TCACAGAGGA AGCTCTGCCT     480
ACTTACCAAA CTATGTTAAA TACTTTGGAT GGAGTTCGTG ATGAAACAGG TGCCAGCCTT     540
ACTTCCTGGG CAATTTGGAC AAGGGCATGG ACTGCTGAAG AAAACAGACA CGGTGATCTT     600
CTTAACAAAT ATCTGTACTT GAGTGGACGA GTTGACATGA AACAAATTGA GAAGACAATT     660
CAGTACCTTA TTGGGTCTGG GATGGATCCT CGGACCGAGA ACAGCCCCTA CCTTGGTTTC     720
```

| | | | | | | |
|---|---|---|---|---|---|---|
| ATTTACACTT | CATTTCAAGA | GAGGGCAACC | TTCATATCCC | ACGGAAACAC | GGCCAGGCTT | 780 |
| GCGAAGGAGC | ATGGTGACAT | AAAATTGGCA | CAGATCTGCG | GCATGATTGC | CTCAGATGAG | 840 |
| AAGCGCCACG | AGACTGCATA | CACAAAGATA | GTGGAAAAGC | TGTTTGAGGT | TGATCCTGAT | 900 |
| GGTACAGTTA | TGGCATTTGC | CGACATGATG | AGGAAGAAGA | TTGCTATGCC | AGCACACCTT | 960 |
| ATGTATGACG | GCCGCGACGA | CAACCTGTTT | GATAACTACT | CTGCCGTCGC | GCAGCGCATT | 1020 |
| GGGGTCTACA | CTGCAAGGA | CTATGCTGAC | ATACTCGAAT | TTCTGGTGGG | GAGGTGGAAG | 1080 |
| GTGGAGCAGC | TAACCGGACT | TTCAGGTGAG | GGAAGAAAGG | CTCAGGAATA | CGTTTGTGGG | 1140 |
| CTGCCACCAA | GAATCAGAAG | GTTGGAGGAG | AGAGCTCAAG | CAAGAGGCAA | GGAGTCGTCA | 1200 |
| ACACTTAAAT | TCAGTTGGAT | TCATGACAGG | GAAGTACTAC | TCTAAATGCT | TGCACCAAGG | 1260 |
| GAGGAGCATG | GTGAATCTTC | CAGCAATACC | ATTCTGAGAA | ATGTTGAATA | GTTGAAAATT | 1320 |
| CAGTTTGTCA | TTTTATCTT | TTTTTCTCC | TGTTTTTGG | TCTTATGTTA | TATGCCACTG | 1380 |
| TAAGGTGAAA | CAGTTGTTCT | TGCATGGTTC | GCAAGTTAAG | CAGTTAGGGG | CAGCTGTAGT | 1440 |
| ATTAGAAATG | CTATTTTTG | TTTCCCTTTT | CTGTGGTAGT | GATGTCTGTG | GAAGTATAAG | 1500 |
| TAAACGTTTT | TTTTTCTCT | GGCAATTTTG | ATGATAAAGA | AAATTTAGTT | CTAAAAACCG | 1560 |
| TCGCACCTTC | CCTGAGGCTT | CTCTTGTCTG | TCGCGAGTGA | CCATGGTGAG | GGTTAGTGTG | 1620 |
| CTGAACGATG | CTCTGAAGAG | CATGTACAAT | GCTGAGAAAA | GGGGAAAGCG | CCAAGTCATG | 1680 |
| ATTCGGCCAT | CCTCCAAAGT | CATTATCAAA | TTCCTTTTGG | TGATGCAGAA | GCACGGATAC | 1740 |
| ATTGGAGAGT | TTGAGTATGT | TGATGACCAC | AGGGCTGGTA | AAATCGTGGT | TGAATTGAAC | 1800 |
| GGTAGACTGA | ACAAGTGTGG | GGTTATTAGT | CCCCGTTTTG | ATGTCGGCGT | CAAAGAGATT | 1860 |
| GAAGGTTGGA | CTGCTAGGCT | TCTCCCCTCA | AGACAGTTTG | GGTATATTGT | ATTGACTACC | 1920 |
| TCTGCCGGCA | TCATGGATCA | CGAAGAAGCT | AGGAGAAAAA | ATGTTGGTGG | TAAGGTACTG | 1980 |
| GGTTTCTTCT | ACTAGAGTTT | AATTTCGATT | AAGAGGATGT | CAGGAATTTC | AATTGAGATT | 2040 |
| CATGGATTGT | AATGGAGGAT | ATGCTAGGCC | CCTAGTAATA | TCAAGCATAG | CAGGAGCTGT | 2100 |
| TTTGTGATGT | TCCTTATTTT | GTTTGCAAAA | CCAAGTTGGT | AACTATAACT | TTTATTTTCT | 2160 |
| TTTATCATTA | TTTTTCTTTA | TACCAAAATG | TACTGGCCAA | GTTGTTTTAA | ACAGTGAGAA | 2220 |
| CTTTGATTAG | AAAAAAAAAA | AAA | | | | 2243 |

( 2 ) INFORMATION FOR SEQ ID NO:2:

( i ) SEQUENCE CHARACTERISTICS:
        ( A ) LENGTH: 216 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Glycine max
        ( B ) STRAIN: Cultivar Wye
        ( D ) DEVELOPMENTAL STAGE: Developing seeds ( v i i ) IMMEDIATE SOURCE:
        ( A ) LIBRARY: cDNA to mRNA
        ( B ) CLONE: pDS4a ( i x ) FEATURE:
        ( A ) NAME/KEY: non-coding sequence
        ( B ) LOCATION: 1..216
        ( D ) OTHER INFORMATION: /note= "IDENTIFICATION METHOD=Homology of clones
pDS4a and pDS1 and similarity of sequence in
SEQ ID NO:1 to 3'non-coding ( x i ) SEQUENCE DESCRIPTION: SEQ ID NO:2:

| | | | | | |
|---|---|---|---|---|---|
| GAAATGTTGA | ATAGTTGAAA | ATTCAGTTTG | TCATTTTTAT | CTTTTATTTT | TTCTCCTTTT | 60 |
| TTGGTCTTTG | TTATATGTCA | CTGTAAGGTG | AAGCAGTTGT | TCTTGCATGG | TTCGCAAGTT | 120 |
| AAGCAGTTAG | GGGCAGCTGT | AGTATTAGAA | ATGGTATTTT | TTTTTTGTT | TTCGCTTTTC | 180 |
| TCTGTGGTAG | TGATGTCTGT | CGAAGTATAA | GTAAAC | | | 216 |

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Glycine max
        ( B ) STRAIN: Cultivar wye
        ( D ) DEVELOPMENTAL STAGE: Developing seeds ( i x ) FEATURE:
        ( A ) NAME/KEY: Protein
        ( B ) LOCATION: 1..16
        ( D ) OTHER INFORMATION:/note= "IDENTIFICATION
            METHOD=N- terminal amino acid
            sequencing"

( x i ) SEQUENCE DESCRIPTION: SEQ ID NO:3:

Arg Ser Gly Ser Lys Glu Val Glu Asn Ile Lys Lys Pro Phe Thr Pro
1               5                   10                  15

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) NAME/KEY: Coding sequence
        ( B ) LOCATION: 1..36

( x i ) SEQUENCE DESCRIPTION: SEQ ID NO:4:

AARGARGTNG ARAAYATHAA RAARCCNTTY ACNCCN                      36

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -

(B) LOCATION: 1..27
(D) OTHER INFORMATION:/note= "N at positions 3,6,9 and 27 is deoxyinosine"

(xi) SEQUENCE DESCRIPTION: SEQ ID NO:5:

GGNGTNAANG GCTTCTTRAT RTTYTCNACN TCCTT                35

(2) INFORMATION FOR SEQ ID NO:6:

(i) SEQUENCE CHARACTERISTICS:
      (A) LENGTH: 391 amino acids
      (B) TYPE: amino acid
      (C) STRANDEDNESS: unknown
      (D) TOPOLOGY: linear (ii) MOLECULE TYPE: protein (xi) SEQUENCE DESCRIPTION: SEQ ID NO:6:

```
Met  Ala  Leu  Arg  Leu  Asn  Pro  Ile  Pro  Thr  Gln  Thr  Phe  Ser  Leu  Pro
 1               5                    10                            15

Gln  Met  Pro  Ser  Leu  Arg  Ser  Pro  Arg  Phe  Arg  Met  Ala  Ser  Thr  Leu
              20                    25                       30

Arg  Ser  Gly  Ser  Lys  Glu  Val  Glu  Asn  Ile  Lys  Lys  Pro  Phe  Thr  Pro
         35                    40                       45

Pro  Arg  Glu  Val  His  Val  Gln  Val  Thr  His  Ser  Met  Pro  Pro  Gln  Lys
    50                       55                    60

Ile  Glu  Ile  Phe  Lys  Ser  Leu  Glu  Asp  Trp  Ala  Asp  Gln  Asn  Ile  Leu
65                       70                    75                            80

Thr  His  Leu  Lys  Pro  Val  Glu  Lys  Cys  Trp  Gln  Pro  Gln  Asp  Phe  Leu
                   85                    90                            95

Pro  Asp  Pro  Ser  Ser  Asp  Gly  Phe  Glu  Glu  Gln  Val  Lys  Glu  Leu  Arg
              100                       105                      110

Glu  Arg  Ala  Lys  Glu  Ile  Pro  Asp  Asp  Tyr  Phe  Val  Val  Leu  Val  Gly
         115                       120                      125

Asp  Met  Ile  Thr  Glu  Glu  Ala  Leu  Pro  Thr  Tyr  Gln  Thr  Met  Leu  Asn
    130                       135                      140

Thr  Leu  Asp  Gly  Val  Arg  Asp  Glu  Thr  Gly  Ala  Ser  Leu  Thr  Ser  Trp
145                       150                      155                       160

Ala  Ile  Trp  Thr  Arg  Ala  Trp  Thr  Ala  Glu  Glu  Asn  Arg  His  Gly  Asp
                   165                       170                      175

Leu  Leu  Asn  Lys  Tyr  Leu  Tyr  Leu  Ser  Gly  Arg  Val  Asp  Met  Lys  Gln
              180                       185                      190

Ile  Glu  Lys  Thr  Ile  Gln  Tyr  Leu  Ile  Gly  Ser  Gly  Met  Asp  Pro  Arg
         195                       200                      205

Thr  Glu  Asn  Ser  Pro  Tyr  Leu  Gly  Phe  Ile  Tyr  Thr  Ser  Phe  Gln  Glu
    210                       215                      220

Arg  Ala  Thr  Phe  Ile  Ser  His  Gly  Asn  Thr  Ala  Arg  Leu  Ala  Lys  Glu
225                       230                      235                       240

His  Gly  Asp  Ile  Lys  Leu  Ala  Gln  Ile  Cys  Gly  Met  Ile  Ala  Ser  Asp
                   245                       250                      255

Glu  Lys  Arg  His  Glu  Thr  Ala  Tyr  Thr  Lys  Ile  Val  Glu  Lys  Leu  Phe
              260                       265                      270

Glu  Val  Asp  Pro  Asp  Gly  Thr  Val  Met  Ala  Phe  Ala  Asp  Met  Met  Arg
         275                       280                      285

Lys  Lys  Ile  Ala  Met  Pro  Ala  His  Leu  Met  Tyr  Asp  Gly  Arg  Asp  Asp
    290                       295                      300

Asn  Leu  Phe  Asp  Asn  Tyr  Ser  Ala  Val  Ala  Gln  Arg  Ile  Gly  Val  Tyr
```

```
305                    310                    315                    320
Thr Ala Lys Asp Tyr Ala Asp Ile Leu Glu Phe Leu Val Gly Arg Trp
                325                    330                    335
Lys Val Glu Gln Leu Thr Gly Leu Ser Gly Glu Gly Arg Lys Ala Gln
                340                    345                    350
Glu Tyr Val Cys Gly Leu Pro Pro Arg Ile Arg Arg Leu Glu Glu Arg
                355                    360                    365
Ala Gln Ala Arg Gly Lys Glu Ser Ser Thr Leu Lys Phe Ser Trp Ile
                370                    375                    380
His Asp Arg Glu Val Leu Leu
385                    390
```

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: linear ( i i ) MOLECULE TYPE: protein ( x i ) SEQUENCE DESCRIPTION: SEQ ID NO:7:

```
Lys Glu Val Glu Asn Ile Lys Lys Pro Phe Thr Pro
1                   5                      10
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
ACTTCGCGGC CGCATGGCTT CCACCCTCCG                                        30
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
CTTCGCGGCC GCTTAGAGTA GTACTTCCCT                                        30
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CCAGAAGATT GAGATTTTCA                                                   20
```

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CCAGAAGATT GAGATTTTCG 20

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GCCAACTTTA TATCGCCG 18